United States Patent
Degertekin et al.

(10) Patent No.: US 11,641,168 B2
(45) Date of Patent: May 2, 2023

(54) PARAMETRIC RESONATOR FOR ELECTRICAL TRANSDUCTION

(71) Applicant: Georgia Tech Research Corporation, Atlanta, GA (US)

(72) Inventors: Fahrettin Levent Degertekin, Atlanta, GA (US); Sarp Satir, Atlanta, GA (US); Sushruta Surappa, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 1297 days.

(21) Appl. No.: 16/038,137

(22) Filed: Jul. 17, 2018

(65) Prior Publication Data

US 2019/0044459 A1    Feb. 7, 2019

Related U.S. Application Data

(60) Provisional application No. 62/533,285, filed on Jul. 17, 2017.

(51) Int. Cl.
| | |
|---|---|
| *H02N 2/18* | (2006.01) |
| *G01N 29/24* | (2006.01) |
| *H02J 50/15* | (2016.01) |
| *A61N 1/378* | (2006.01) |

(52) U.S. Cl.
CPC ......... *H02N 2/188* (2013.01); *G01N 29/2406* (2013.01); *H02J 50/15* (2016.02); *A61N 1/3787* (2013.01); *G01N 2291/02827* (2013.01)

(58) Field of Classification Search
CPC ..... H02N 2/188; G01N 29/2406; H02J 50/15; A61N 1/3787
See application file for complete search history.

(56) References Cited

U.S. PATENT DOCUMENTS

| | | | |
|---|---|---|---|
| 6,628,124 B1* | 9/2003 | Yamagata | G01L 1/144 324/633 |
| 8,974,366 B1* | 3/2015 | Radziemski | A61N 1/37217 600/16 |
| 11,264,982 B2* | 3/2022 | Terenzi | G01N 27/4163 |
| 2001/0010174 A1* | 8/2001 | Matsiev | G01H 13/00 73/64.53 |
| 2003/0041653 A1* | 3/2003 | Matsiev | G01H 13/00 73/54.25 |
| 2009/0048544 A1* | 2/2009 | Rybyanets | A61N 7/02 601/2 |
| 2010/0158285 A1* | 6/2010 | Pompei | B82Y 30/00 381/191 |

(Continued)

*Primary Examiner* — Daniel Kessie
*Assistant Examiner* — Brian K Baxter
(74) *Attorney, Agent, or Firm* — Troutman Pepper Hamilton Sanders LLP; Ryan A. Schneider; Ginger G. Turner

(57) ABSTRACT

A parametric resonator can be driven by varying a parameter of a modulated capacitor or other externally powered type device to achieve transduction. Conventionally, externally powered type devices generally require an external power source or a static charge to achieve transduction. By pumping the parameter of the device at a frequency that is about twice the resonance frequency, and an amplitude that is above a threshold, however parametric resonance can be generated and sustained without requiring an external power source or charge to be applied to the device.

20 Claims, 15 Drawing Sheets

(56) References Cited

U.S. PATENT DOCUMENTS

| | | | |
|---|---|---|---|
| 2012/0176609 A1* | 7/2012 | Seppa | G01S 13/753 257/E27.122 |
| 2012/0300593 A1* | 11/2012 | Perry | H02J 7/00034 367/181 |
| 2013/0116568 A1* | 5/2013 | Gerton | A61B 8/14 600/443 |
| 2013/0178915 A1* | 7/2013 | Radziemski | H02J 7/00034 607/61 |
| 2014/0288428 A1* | 9/2014 | Rothberg | G01S 15/8915 600/443 |
| 2015/0280484 A1* | 10/2015 | Radziemski | H02J 50/90 320/108 |
| 2015/0326034 A1* | 11/2015 | Perry | B06B 1/0207 307/104 |
| 2015/0333798 A1* | 11/2015 | Perry | H02J 50/402 320/108 |
| 2015/0333799 A1* | 11/2015 | Perry | H02J 50/15 320/108 |
| 2015/0333800 A1* | 11/2015 | Perry | H02J 50/15 320/108 |
| 2016/0268813 A1* | 9/2016 | Reynolds | G10K 11/346 |
| 2017/0023511 A1* | 1/2017 | Wilkinson | G01N 27/4163 |
| 2017/0182852 A1* | 6/2017 | Makin | H02J 50/402 |
| 2017/0319858 A1* | 11/2017 | Radziemski | A61B 8/14 600/443 |
| 2017/0363581 A1* | 12/2017 | Makin | G01H 13/00 73/54.25 |
| 2018/0085605 A1* | 3/2018 | Maharbiz | G01H 13/00 73/64.53 |
| 2019/0199139 A1* | 6/2019 | Perry | B82Y 30/00 381/191 |
| 2019/0313908 A1* | 10/2019 | Melodia | G01S 13/753 257/E27.122 |
| 2020/0257136 A1* | 8/2020 | Arbabian | G01L 1/144 324/633 |

* cited by examiner

PARAMETRIC RESONATOR FOR ELECTRICAL TRANSDUCTION

CROSS-REFERENCE TO RELATED APPLICATIONS

This application claims priority under 35 U.S.C. § 119(e) to U.S. Provisional Patent Application No. 62/533,285, "Ultrasonic Transducers Using Parametric Resonance" filed Jul. 17, 2017 which is hereby incorporated by reference herein in their entireties as if fully set forth below.

STATEMENT REGARDING FEDERALLY SPONSORED RESEARCH OR DEVELOPMENT

This invention was made with government support under Grant EB019098 awarded by the National Institutes of Health. The government has certain rights in the invention.

BACKGROUND OF THE INVENTION

This disclosure relates generally to electrical circuits, and more particularly to parametric resonators and electrical transducers.

A parametric resonator can be generally described as a driven harmonic oscillator in which the oscillations are driven by varying a physical parameter of a system element at a pump frequency to induce oscillations in the system. A simple example of a parametric oscillator is a child pumping a swing in motion by periodically standing and squatting at key points in the swing arc to change the moment of inertia of the swing. An analogue example of direct resonance is the child rocking back and forth to pump the swing. While rocking back and forth, the child can cause the swing to move even if the swing is at rest; however, standing and squatting while the swing is at rest only alters a physical parameter of the swing and does not by itself initiate oscillations.

In electronics, parametric resonators can be driven by varying a parameter of an electrical component at about twice the resonance frequency of the resonance circuit to generate an electrical signal oscillating at the resonance frequency. One of the earliest studies of parametric resonance in an electrical circuit was conducted by George Francis FitzGerald who, in 1892 tried to excite oscillations in a resonant circuit (LC circuit) by pumping the circuit by varying an inductance provided by a dynamo, a known electromechanical generator.

Applications for such systems proved limited, however, and direct resonance (where the drive signal has a frequency about equal to the resonance frequency) persists as the primary means by which resonance is achieved in electrical circuits. Many challenges of designing electrical parametric oscillators stem from the highly non-linear behavior of parametric oscillators. For example, a parametric oscillator having a zero-amplitude electrical current will remain so, even while the parameter is pumped, a problem recognized in the early studies and solved by utilizing a dynamo which both functioned to provide the variable parametric value and supply an electrical current to facilitate parametric resonance. In contrast, even with an initial zero amplitude, an electrical signal driven by direct resonance can increase in amplitude linearly over time. Because direct resonance is a linear phenomenon, electrical circuit design is therefore more straight forward compared to design based on parametric resonance.

Much more recently, one study (N. B. Caldwell and M. F. Daqaq, Appl. Phys. Lett. 110, 093903, 2017) revisited the concept of electrical circuit parametric oscillators in relation to producing parametric resonance in a vibratory energy harvesting system. The design uses a variable inductor to induce parametric resonance in the harvesting circuit. Similar to the earliest studies, the inductance was varied by movement of a magnet in relation to the inductive coil, thereby inducing an electrical current in the inductor in addition to simply varying the inductance. The inductive coil used in the study consists of 1100 windings of 28 gauge copper wire; the weight and size of which is approximately that of a brick and is therefore not suitable for modern portable electronic design. In general, inductive parametric transducers are quite bulky, and as electronics have historically scaled down in size, challenges in designing miniaturized inductive elements persist.

Therefore, even though it was theorized early on that parametric resonance could be utilized in electrical circuits in certain energy-related applications, numerous other avenues have been explored with little advancement in the way of parametric resonance.

Take, for example, the challenges of energizing implantable medical devices. Implantable medical devices are used daily by over 25 million US citizens. Low power, relatively large implants such as pacemakers are equipped with non-rechargeable batteries that last a lifetime. However, a tradeoff for longevity is limited available power, which limits the applications of non-rechargeable batteries. For example, non-rechargeable batteries fail to meet power needs of implants for deep brain stimulation, optogenetics, and peripheral nerve stimulation.

Various methods of energizing implantable microdevices have been explored. Energy harvesting from inside the human body is one such method that has gained interest in recent years. By making use of the motion of the heart, muscles and various other organs inside the human body, low powered implants can be energized. However, this method of energy scavenging can have limited applicability to low power applications.

As an alternative to batteries, inductive radio frequency coupling and ultrasonic transduction has applications for wireless power delivery. Inductive and electromagnetic power transfer are currently the most popular techniques employed in powering implanted devices wirelessly. However, a disadvantage of inductive coupling is the limited range of power transfer. As technological advances in other areas of research result in implants to increasingly smaller sizes, antenna size is also reduced thereby reducing the distance over which power can be delivered via inductive coupling. Downsizing inductive coil size also creates challenges when mutually orientating the primary and secondary coils which can adversely affect the efficiency of power transfer.

Far field techniques such as radio frequency power transfer can overcome the distance limitation. However due to the large wavelength of the radio frequency signal, the receiver antenna cannot be miniaturized, and the size of the receiver antenna can be prohibitive for very small sized implants. Operating at greater frequency can allow for smaller antenna design compared to radio frequency antennas, however the absorption of higher frequency electromagnetic radiation in human tissue is much greater. Additionally, electromagnetic energy cannot be focused to a small spot size as this can cause overheating of the tissue.

Ultrasound power transfer can overcome many of the limitations faced by inductive power transfer. Because ultrasound travels at the speed of sound, electromagnetic radiation travels at the speed of light, and the speed of sound is much lower than the speed of light, ultrasound has much smaller wavelengths when compared to electromagnetic radiation; hence it is possible to operate at lower frequencies, focus to a small spot more efficiently, and thereby improve the coupling efficiency between the source and the implant. The permissible intensity level as approved by the Food and Drug Administration (FDA) is much greater for ultrasound (7.2 mW/mm$^2$) as compared to radio frequency electromagnetic radiation (100 µW/mm$^2$) used for transferring wireless power. Hence ultrasound has the capability of delivering much more power into the human body via this method.

Ultrasonic transducers have been in use for many years for various applications such as medical imaging, non-destructive testing, wireless power transfer, and sensors. Almost all ultrasonic transducers can be classified as either piezoelectric transducers (utilizing piezoelectric devices) or capacitive transducers (utilizing modulated capacitors). Compared to piezoelectric ultrasonic transducers, capacitive ultrasonic transducers are easier to integrate into electronics by being able to be fabricated together with other system electronics on a semiconductor substrate. However, despite the integration advantages of capacitive transducers, piezoelectric transducers are used almost exclusively for ultrasonic wireless power transfer. This is because a piezoelectric device is self generating, meaning it generates an electrical current in response to a mechanical stimulus, whereas a modulated capacitor is typically an externally powered type device, meaning a permanent charge or an applied voltage such as a DC bias is required in conventional systems to generate an electrical signal and the modulated capacitor doesn't itself produce an electrical signal. One strategy to remove the need for an applied voltage on a capacitive electromagnetic transducer is to utilize electret films to provide a pre-charged electrode; however the long term reliability of these devices is yet to be studied.

Although the above discussion is related to the medical field, as will be appreciated and understood challenges of wireless sensing and power transfer persists in many applications.

BRIEF SUMMARY OF THE INVENTION

Systems, devices, and methods disclosed herein can generally include externally powered type transducer that can function as a pump for a parametric resonator electrical circuit, and the parametric resonator can sustain a resonating electrical signal absent a DC bias, electrical charge, or other external power source applied to the transducer. Such systems, devices, and methods can have applications in many fields, including some of the example implantable medical device applications shown herein wherein a capacitive micromachined ultrasonic transducer can be used as a pump for a parametric resonator to convert acoustic energy from an ultrasonic source to a sustained electrical signal.

An example electronic device can be configured to sustain an electrical signal responsive to varying a capacitance of a capacitor without requiring a permanent charge or a voltage applied to the capacitor. The electronic device can be further configured to generate the electrical signal responsive to varying the capacitance without requiring a permanent charge or a voltage applied to the capacitor. The capacitance can be varied in response to a mechanical force. The electronic can be configured to sustain the electrical signal responsive to varying the capacitance at frequency that is between about 16 kHz and 100 MHz. The electronic device can be configured to oscillate the electrical signal at an electrical resonance frequency responsive to varying the capacitance at a pump frequency that is equal to about twice the electrical resonance frequency.

The electronic device can be configured to sustain the electrical signal responsive to varying the capacitance of the capacitor between a first capacitance that is equal to an average capacitance plus a change in capacitance and a second capacitance that is equal to the average capacitance minus the change in capacitance, wherein the change in capacitance is equal to or greater than about twice the average capacitance divided by a quality factor of the electronic device. The average capacitance can be a function of a mechanical force acting to vary the capacitance of the capacitor. The electronic device can form at least a portion of an implantable medical device. The capacitor can have a mechanical resonance frequency equal to about twice an electrical resonance frequency of the electronic device.

An example parametric resonator can comprise an electronic device that can be an externally powered device such as a modulated capacitor. The electronic device can have an electrical parameter that varies in response to an external force, and the parametric resonator can be configured to sustain an oscillating electrical signal in response to varying the electrical parameter without requiring an electrical power source to sustain the oscillating electrical signal.

The parametric resonator can be configured to oscillate the electrical signal at a resonance frequency responsive to varying the electrical parameter at a pump frequency that is about twice the resonance frequency. The pump frequency can be between about 16 kHz and 100 MHz. The variable electrical parameter can be a capacitance value. The electronic element is a modulated capacitor and the electrical parameter is capacitance. The parametric resonator can be configured to sustain the oscillating electrical signal in response to varying the capacitance of the modulated capacitor with the application of an acoustic signal to the modulated capacitor, and a frequency of the acoustic signal can be about twice a frequency of the oscillating electrical signal. The acoustic signal can vary the capacitance of the modulated capacitor between a first capacitance that is equal to an average capacitance plus a change in capacitance and a second capacitance that is equal to the average capacitance minus the change in capacitance, wherein the change in capacitance is equal to or greater than about twice the average capacitance divided by a quality factor of the electronic device.

An example method for electrical transduction can include the steps of applying a force to an electronic device of a parametric resonator, oscillating an electrical parameter of the electronic device at a pump frequency in response to the applying the force, generating parametric resonance in the parametric resonator in response the oscillating the electrical parameter, and sustaining the parametric resonance in the parametric resonator without requiring either a power source or a permanent charge applied to the device. The force applied to the electronic device can be a mechanical force and the electronic device can be a capacitor. The method can further comprise generating the initial oscillation through inductive coupling of the parametric resonator with an electromagnetic signal. The pump frequency at which the electrical parameter oscillates can be about equal to twice a resonance frequency of the parametric resonator.

An example electronic device can be configured to sustain an electrical signal responsive to varying a capacitance of a capacitor absent both a permanent charge and a voltage applied to the capacitor. The electronic device can further be configured to generate the electrical signal responsive to varying the capacitance absent both a permanent charge and a voltage applied to the capacitor. The capacitance can be variable in response to a mechanical force. The capacitor can be a capacitive micromachined ultrasonic transducer. The electronic device can be further configured to sustain the electrical signal responsive to varying the capacitance at a frequency that is between about 16 kHz and 100 MHz. The electronic device can be further configured to sustain the electrical signal oscillating at an electrical resonance frequency responsive to varying the capacitance at a pump frequency that is about equal to twice the electrical resonance frequency. The electronic device of claim 1 can be further configured to sustain the electrical signal responsive to varying the capacitance with an average capacitance value through a change in capacitance, the change in capacitance being about equal or greater than twice the average capacitance divided by a quality factor of the parametric resonator. The average capacitance can be function of a force acting to vary the capacitance of the capacitor. The capacitor can have a mechanical resonance frequency about equal to twice the electrical resonance frequency. The electronic device can form at least a portion of an implantable medical device.

An example system can include an externally powered type device having a variable electrical parameter and a parametric resonator configured to sustain an oscillating electrical signal solely in response to varying the variable electrical parameter. The externally powered type device can be a component in the parametric resonator. The electrical signal in the system can oscillate at a resonance frequency responsive to varying the variable electrical parameter at a pump frequency that is about twice the resonance frequency, and the pump frequency can be an ultrasonic frequency. The variable electrical value can be a capacitance value. The parametric resonator can be configured to sustain the oscillating electrical signal solely in response to varying the variable electrical parameter with an amplitude that is about equal to or greater than twice an average of the variable electrical parameter divided by quality factor of the parametric resonator, and wherein the amplitude is within physical limits of the transducer.

An example method for electrical transduction can include the steps of applying a force to an externally powered type device, oscillating an electrical parameter value of the device between an unstimulated parameter value and a stimulated parameter value at pump frequency in response to the applying the force, generating an initial oscillation in a parametric resonator that includes the device, generating parametric resonator in response to the generating the initial oscillation and the oscillating the parameter value, and sustaining the parametric resonance in the parametric resonator absent both a power source and a permanent charge applied to the device. The force applied to the externally powered type device can be a mechanical force and the device can be a capacitor. The step of generating the initial oscillation can further include generating the initial oscillation absent both a power source and a permanent charge applied to the device. The method can further include, receiving an electromagnetic signal, and generating the initial oscillation through inductive coupling of the parametric resonator with the electromagnetic signal. The pump frequency can be about equal to twice a resonance frequency of the parametric resonator.

An example parametric resonator can sustain an electrical signal responsive to oscillating a capacitance of a capacitive transducer. The parametric resonator can sustain the electrical signal in the absence of both a direct current bias and a permanent charge applied to the transducer. The capacitive transducer can be an externally powered type transducer, and the capacitive transducer can be an electromechanical transducer such as a capacitive micromachined ultrasonic transducer.

The capacitance can be oscillated at a frequency between about 16 kHz and 100 MHz, and the parametric resonator can sustain the electrical signal responsive to capacitive oscillations at a frequency within that range. The capacitance can be oscillated at a frequency that is about twice an electrical resonance frequency of the parametric resonator, and the parametric resonator can sustain the electrical signal oscillating at the electrical resonance frequency.

The parametric resonator can sustain the electrical signal further in response to sustaining a change in capacitance above about twice an average capacitance divided by a quality factor of the parametric resonator. The average capacitance can be a function of a force acting to oscillate the capacitance.

The parametric resonator can form at least a portion of an implantable medical device.

The capacitor can have a mechanical resonance frequency that is about equal to twice the electrical resonance frequency.

An example system can include an externally powered type electrical transducer having a variable electrical parameter, a parametric resonator configured to sustain an oscillating electrical signal solely in response to varying the variable electrical parameter.

The electrical signal can oscillate at a resonance frequency responsive to varying the variable electrical parameter at a pump frequency that is about twice the resonance frequency.

The variable electrical parameter value can be a capacitance value.

The transducer can be an electromechanical ultrasonic transducer.

The parametric resonator can sustain the oscillating electrical signal solely in response to varying the variable electrical parameter with an amplitude that is about equal to or greater than twice an average of the variable electrical parameter divided by a quality factor of the parametric resonator, and wherein the amplitude is within physical limits of the transducer.

An example method for electrical transduction can include the steps of applying a force to an externally powered type electrical transducer, oscillating a parameter value of the transducer between an unstimulated parameter value and a stimulated parameter value at a pump frequency, generating an initial oscillation in a parametric resonator that includes the transducer, generating parametric resonance in the parametric resonator, and sustaining the parametric resonance in the parametric resonator absent a power source applied to the transducer.

The force applied to the transducer can be a mechanical force, and the transducer can be a capacitive electromechanical transducer.

The step of sustaining the parametric resonance can further include sustaining the electrical signal absent a direct current bias or a static charge applied to the transducer.

The method can further include the steps of receiving an electromagnetic signal, and generating the initial oscillation through inductive coupling of the parametric resonator with the electromagnetic signal.

The pump frequency at which the parameter value oscillates can be about equal to twice a resonance frequency of the parametric resonator.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE SEVERAL VIEWS OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION OF THE INVENTION

The components, steps, and materials described hereinafter as making up various elements of the disclosed technology are intended to be illustrative and not restrictive. Many suitable components, steps, and materials that would perform the same or similar functions as the components, steps, and materials described herein are intended to be embraced within the scope of the disclosed technology. Such other components, steps, and materials not described herein can include, but are not limited to, similar components or steps that are developed after development of the disclosed technology.

The examples disclosed herein illustrate devices and systems for driving a parametric resonator by varying a parameter of an externally powered type device to achieve transduction. Conventionally, externally powered type devices generally require an external power source or a static charge to achieve transduction. By pumping the parameter of the device at a frequency that is about twice the resonance frequency, and an amplitude that is above a threshold, however parametric resonance can be generated and sustained without requiring an external power source or charge to be applied to the device.

To illustrate, devices and methods for modulating the capacitance of a capacitive ultrasonic transducer with acoustic waves at ultrasound frequencies to sustain oscillations in a parametric resonance circuit are presented. Such devices are hereafter referred to as a capacitive parametric ultrasound transducer (CPUT). The use of ultrasound can provide a means for wirelessly acting on the transducer, and the use of the parametric resonance circuit in conjunction with the variable capacitor can result in a sustained electrical output without the need for a DC bias or a permanent charge applied to the capacitive ultrasonic transducer, even though the capacitive element is an externally powered type device. Additionally, when driven to an unstable regime, a CPUT can transition into parametric resonance with negligible external electrical stimuli such as radio frequency (RF) interference signals or potentially with the thermal noise in the electrical system providing the initial conditions required for parametric resonance. Further, the capacitive ultrasonic transducer and resonance circuit can be fabricated by standard micromachining techniques, allowing for integration on a semiconductor substrate.

Figure 1:
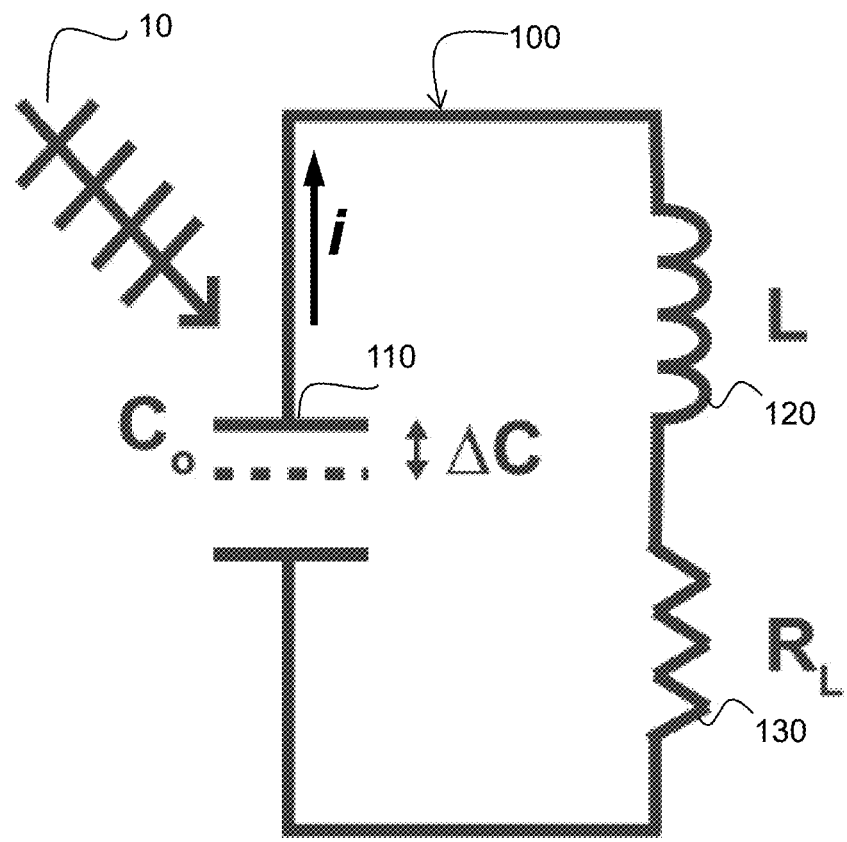
FIG. 1 illustrates a circuit diagram of a system according to the present invention.

FIG. 1 is a simplistic circuit diagram illustrating aspects of operation of an example parametric resonator 100. A linear time varying capacitor 110 is shown in circuit with an inductor 120 representing a reactive circuit impedance and a resistor 130 representing a real circuit impendence. The impedance can be designed such that when connected to the capacitor 110, forms a resonator circuit 100 having a resonance frequency $f_0$. In FIG. 1, the capacitor 110, the inductor 120, and the resistor 130 are connected in series to form an RLC circuit. The capacitor 110 can have an unstimulated parameter value $C_0$ and can have a variable capacitance that can oscillate between stimulated parameter values $C_0 \pm \Delta C$ when pumped by a forcing signal 10. The frequency at which the capacitance oscillates can be determined by a pump frequency of the forcing signal 10, and the stimulated parameter value can be determined by a pump force or an applied forcing amplitude of the forcing signal 10.

As will be appreciated and understood, the variable circuit element could be a variable resistor or variable inductor, for example, and need not be a capacitor; a resistor need not be included to establish resonance; and circuit elements need not be in series.

As illustrated in FIG. 1, the capacitance can be varied at a pump frequency $f_p = 2f_0$ by an incoming ultrasound forcing signal 10. Applying Kirchoff Voltage Law and Kirchoff Current Law to the circuit shown in FIG. 1, results in the following equations:

$$-i = \frac{d}{dt}Q = \frac{d}{dt}CV \quad \text{(Equation 1)}$$

$$V = R_L i + L\frac{d}{dt}i \quad \text{(Equation 2)}$$

where V is the voltage across the capacitor 110, i is the current in the circuit 100, L is the inductance and $R_L$ is the load resistance. Eliminating current from the first equation produces $$\left[\frac{d^2}{dt^2} + \frac{R_L}{L}\frac{d}{dt} + \frac{1}{LC}\right]V = 0 \quad \text{(Equation 3)}$$

which is similar to the response of a damped harmonic oscillator. Modulating the capacitance at the pump frequency $\omega_p=2\pi f_p$, produces $$C = C_0\left[1 - \frac{\Delta C}{C_0}\sin(\omega_p t)\right] \quad \text{(Equation 4)}$$

Then substituting $\omega_0 = 1/\sqrt{LC}$ and assuming $\Delta C \ll C_0$, Equation 3 can be written as, $$C = \left[\frac{d^2}{dt^2} + \frac{R_L}{L}\frac{d}{dt} + \omega_0^2\left[1 - \frac{\Delta C}{C_0}\sin(\omega_p t)\right]\right]V \cong 0 \quad \text{(Equation 5)}$$

Equation 5 is a damped Mathieu equation. When there is a non-zero initial oscillation in the circuit 100 around the frequency $\omega_0$, the pump signal 10 can generate a drive signal around the resonance frequency when $\omega_p \approx \omega_0$. From the solution of Equation 5, it can be observed that when $$\frac{\Delta C}{C_0} > \frac{2R_L}{\omega_0 L} = \frac{2}{Q_{el}},$$

where $Q_{el}$ is the quality factor of the electrical circuit 100, the system can become unstable and a voltage can grow across the capacitor 110. Here $$\frac{\Delta C}{C_0}$$

can be understood as the normalized electrical energy pumped into the system from the external source by changing the capacitance and $$\frac{2}{Q_{el}}$$

represents me normalized energy lost in the oscillator 100 in every cycle. In this example, the changing capacitance can be a function of both time and gap between the two plates of the capacitor, for which a nonlinear Mathieu equation having a stable solution can be obtained. However, for small values of $$\frac{\Delta C}{C_0},$$

the level of forcing required to drive the system into parametric resonance holds for both the linear and nonlinear case.

To further illustrate, a one-dimensional lumped parameter system including the parametric resonator circuit 100 of FIG. 1 is simulated in the time domain using Simulink (The MathWorks Inc., Natick, Mass.). The model is used herein to investigate the threshold behavior of a specific example design for parametric resonance without small signal limitations, and the energy conversion efficiency of the circuit is explored herein in a limited parameter space for illustration purposes. In this illustration, the target ultrasound frequency, or pump frequency $f_p=2f_0$ is chosen to be around 2 MHz. The time varying capacitor is modelled as two parallel plates where one plate is fixed, and the other plate is movable. In the simulation, the area of the movable parallel plate is chosen to be 1 mm², consistent with a size that can be practically implemented. With $6.33\times10^{-7}$ kg mass and $1\times10^8$ N/m spring constant, the dynamics of the plate can be such that a mechanical resonance frequency of 2 MHz can result in large displacements of the spring mass structure. In this one-dimensional example the effect of the fluid medium is included using the acoustic impedance for a plane wave in water ($Z_f=\rho c A$, $\rho$: density, c: speed of sound, A: area of the moving plate). With this acoustic forcing signal 10, the mechanical quality factor is calculated to be roughly around 5. Assuming 120 nm gap between the plates to form the capacitor 110, $C_0$, the values of the inductance (L=340 μH) and load resistance ($R_L=50\Omega$) are chosen such that the undisturbed resonant frequency ($f_0$) of the electric circuit 100 is 1 MHz with $Q_{el}$ of 43. With this idealized model, the parametric resonance threshold behavior is investigated with results summarized in FIGS. 2A-2D.

Figure 2A:
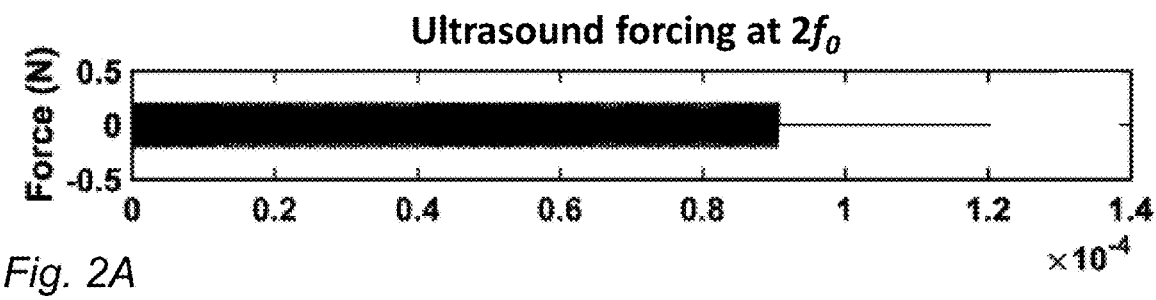
FIGS. 2A-D and 3 illustrate simulation results of operational aspects of the system of FIG. 1 according to the present invention.
Figure 2B:
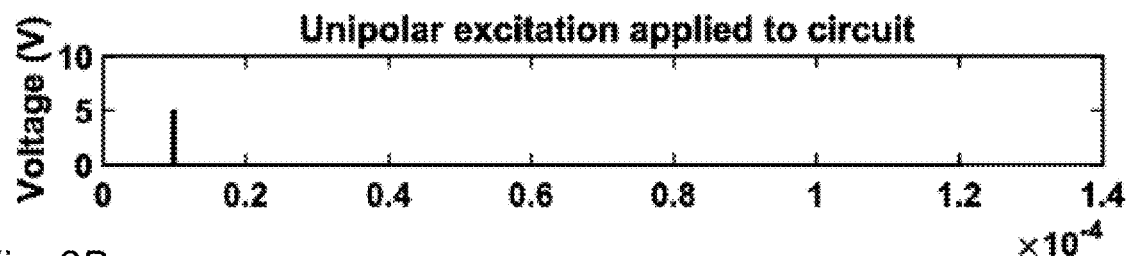
Figure 2C:
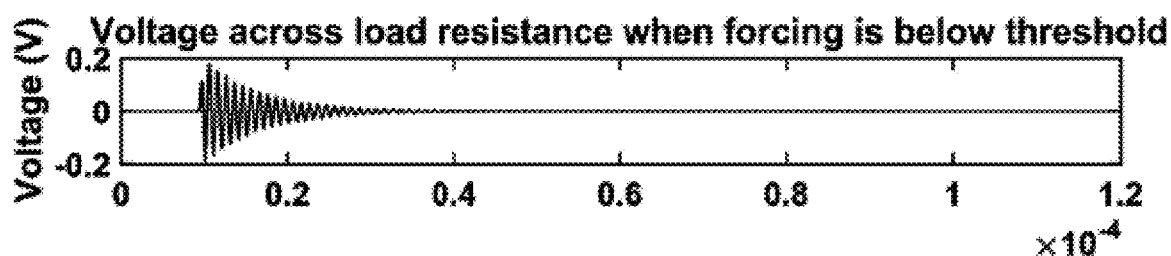
Figure 2D:
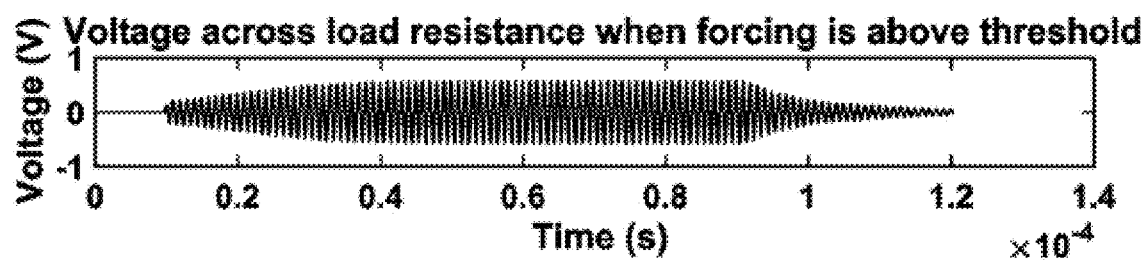

FIG. 2A illustrates a forcing signal 10 providing an applied forcing amplitude to the plate of the simulated capacitor 110 at a pump frequency of $2f_0$ consistent with a forcing signal that can be provided by an ultrasonic source. FIG. 2B shows a short unipolar voltage pulse applied across the electrical circuit 100 to induce some initial oscillation at about 10 μs. FIGS. 2C and 2D show the effect of the magnitude of the applied forcing amplitude on the response of the system as indicated by the voltage on the load resistor 130. In both FIGS. 2C and 2D, voltage across the load resistance $R_L$ begins to oscillate when the unipolar pulse is applied across the electrical circuit 100 as illustrated in FIG. 2B. FIG. 2C illustrates a decaying oscillating voltage across RI, when the applied forcing amplitude does not produce a change in capacitance required for parametric resonance.

Increasing the applied forcing amplitude to the transducer can result in sustained oscillations. As illustrated in FIG. 2D, once the applied forcing amplitude is greater than a threshold forcing amplitude, the current in the circuit 100 can phase lock with the forcing signal 10 and a voltage across the load resistance 130 can grow, thereby transferring energy from the ultrasonic forcing signal 10 to the load resistance 130. The nonlinearities present in the system eventually cause the voltage across the resistor 130 to attain a steady-state value. When the forcing signal 10 is stopped, (as shown at around 90 μs in the simulation) the voltage across the load resistor can decay.

The efficiency for converting acoustic energy to electrical energy can vary with different parameters such as load resistance, level of forcing, receiver dynamics, forcing frequency, and incident ultrasonic field distribution, for example. Here, by way of demonstration, the variation of the pump frequency and the applied forcing amplitude is explored using the one-dimensional model including the parametric resonator 100 driven by the modulated capacitor 110 illustrated in FIG. 1. As illustrated in Equation 6, the acousto-electrical conversion efficiency can be defined as the ratio of the time averaged power dissipated across the resistor 130 to the available acoustic power.

$$\text{Acousto-electrical conversion efficiency} = \frac{\frac{1}{T}\int i^2 R_L dt}{I_{ac} \times A} \times 100(\%) \quad \text{(Equation 6)}$$

Figure 3:
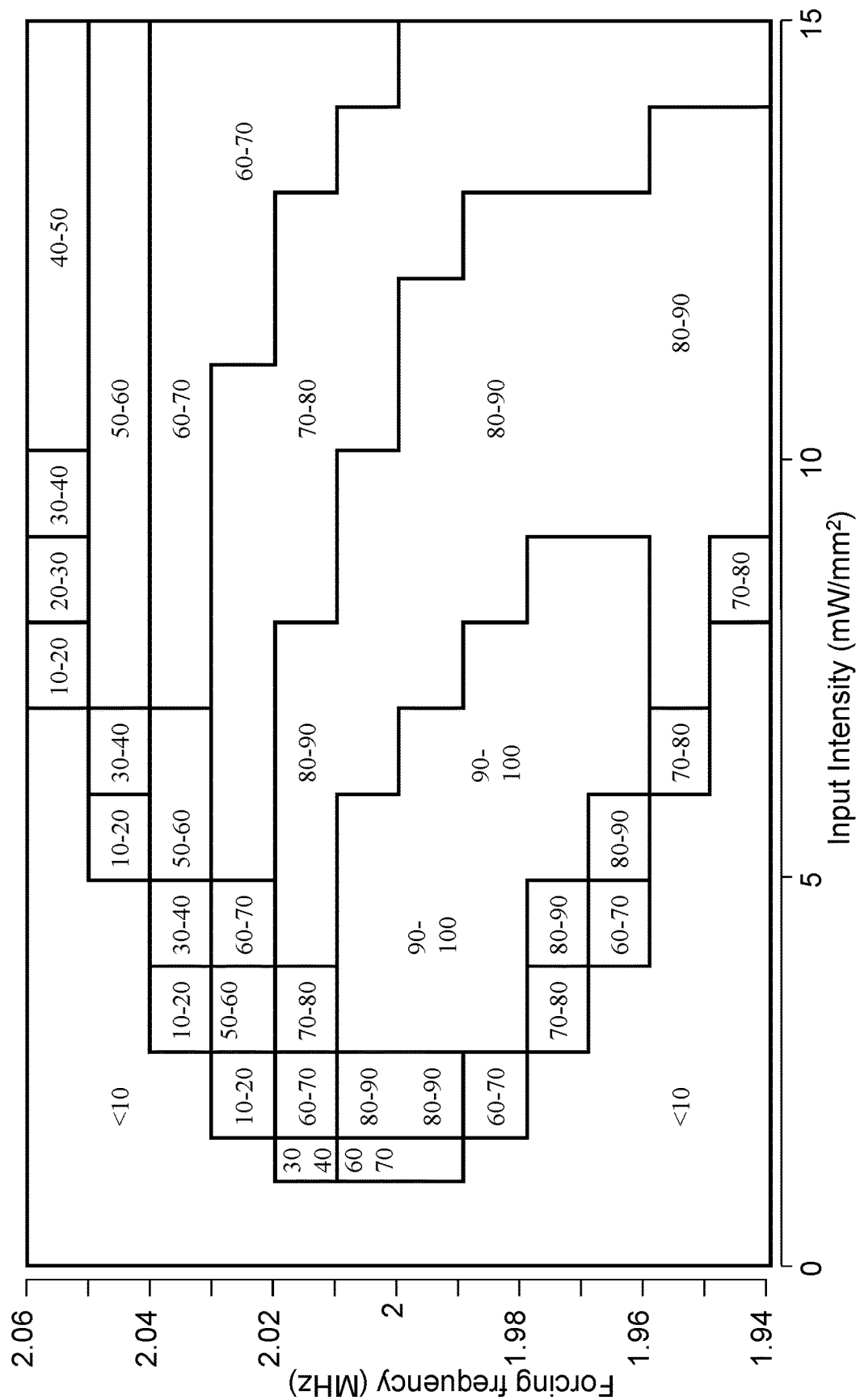

Here, i is the current, $R_L$ is the load resistance 130, $I_{ac}$ is the acoustic intensity, or applied forcing amplitude incident at the surface of the plate of the capacitor 110, and A is the area of the moving plate as defined above. The two-dimensional map in FIG. 3 shows a variation of conversion efficiency with incident acoustic intensity and ultrasound pump frequency for a fixed load resistance of 50Ω, which illustrates the complex nature of the system. The acoustic intensity threshold, or threshold forcing amplitude for sustaining parametric resonance, can depend on the pump frequency, and it can be minimized at a mechanical resonance frequency. The simulation calculates a maximum acousto-electrical conversion efficiency over 99% (corresponding to ~0 dB insertion loss) at a pump frequency of 1.99 MHz and an applied forcing amplitude of 4 mW/mm², indicating that selection of electrical parameters of the system can provide a near perfect mechanical to electrical impedance match to the fluid medium, effectively transforming the load resistance into real valued acoustic impedance. The simulation results in FIG. 3 show the efficiency reducing gradually with increasing acoustic intensity at this frequency, but remaining over 70% in a wide range of intensity values above 4 mW/mm².

At greater applied acoustic intensity, the average value of the capacitance $C_0$ can gradually increase due to the nonlinear nature of electrostatic forces and can effectively detune the electrical and mechanical resonance frequencies thereby reducing efficiency. Such nonlinearities can explain the slight shift of the pump frequency at which maximum efficiency is observed from the initial design frequency of 2 MHz to 1.99 MHz. In the case wherein the resonance circuit utilizes a reactive circuit element such as a capacitor or an inductor, because the level of applied forcing amplitude on the transducer can affect the value of the mean modulated reactance, to achieve better frequency matching between a desired force input at $2f_0$ and a resonator circuit, and to achieve desired $Q_{el}$ of the resonator circuit, the circuit resonance frequency $f_0$ can be based on the mean modulated reactance for the desired force input.

FIG. 3 also shows, that for the example simulation, the bandwidth of the simulated CPUT is narrow, about 70 to 80 kHz centered at a pump frequency of 1.99 MHz and an applied forcing amplitude of 4 mW/mm², and the bandwidth broadens as the applied forcing amplitude increases. In general, the simulations show that when resonances of the mechanical and electrical systems are matched and the parametric resonance condition is met with input forcing and quality factor adjustments, the CPUT can be a high efficiency energy conversion device. It is contemplated that similar results can be obtained with any electrical externally powered type modulated device with a variable parameter value that is designed with a resonator circuit and forced by a mechanical or other system using the design principals outlined here.

CPUT operation in air is contemplated. It is expected that CPUT operation should not be different in air so long as resonance forcing conditions are met, with possibly better operation when designed for lower forcing frequencies. In air the frequencies of an incident acoustic wave can be on the order of 1 kHz to 200 kHz, so that the attenuation does not result in a reduction in forcing amplitude below levels at which externally powered type modulated devices would be able to sustain resonance within a parametric resonance circuit. Similarly, for medical implants, the pump frequency can be from 100 kHz to 20 MHz or above depending on the depth of the device in the body. Further generalizations for CPUT and other externally powered type device driven parametric resonators are contemplated for use in different media and for different applications. Specific implementations of such variations can require an in-depth analysis in terms of impedance matching, mechanical and acoustic design, and diffraction effects including incidence angle variations.

Proof-of-principle experiments are presented using a micromachined capacitor ultrasonic transducer (CMUT) as a time varying reactance in a CPUT. In the experiments, the CMUT includes an array of 80 square membranes, each membrane having an edge length of 46 μm, fabricated on a silicon substrate. A bottom electrode common to the membranes is made by sputtering Chromium, and AlSi deposited on the membrane acts as the top electrode. The membranes are made from $Si_3N_4$ deposited by a plasma-enhanced chemical vapor deposition process and are about 2 μm thick. The effective gap between the suspended membrane and the substrate is approximately 120 nm. The membranes are then electrically connected in parallel to increase the total capacitance.

The fabrication and characterization of CMUT arrays is known; however, CMUT arrays were originally fabricated for imaging applications with a center frequency of 7 MHz in water and such devices are not optimized to function as a CPUT driver.

Figure 4:
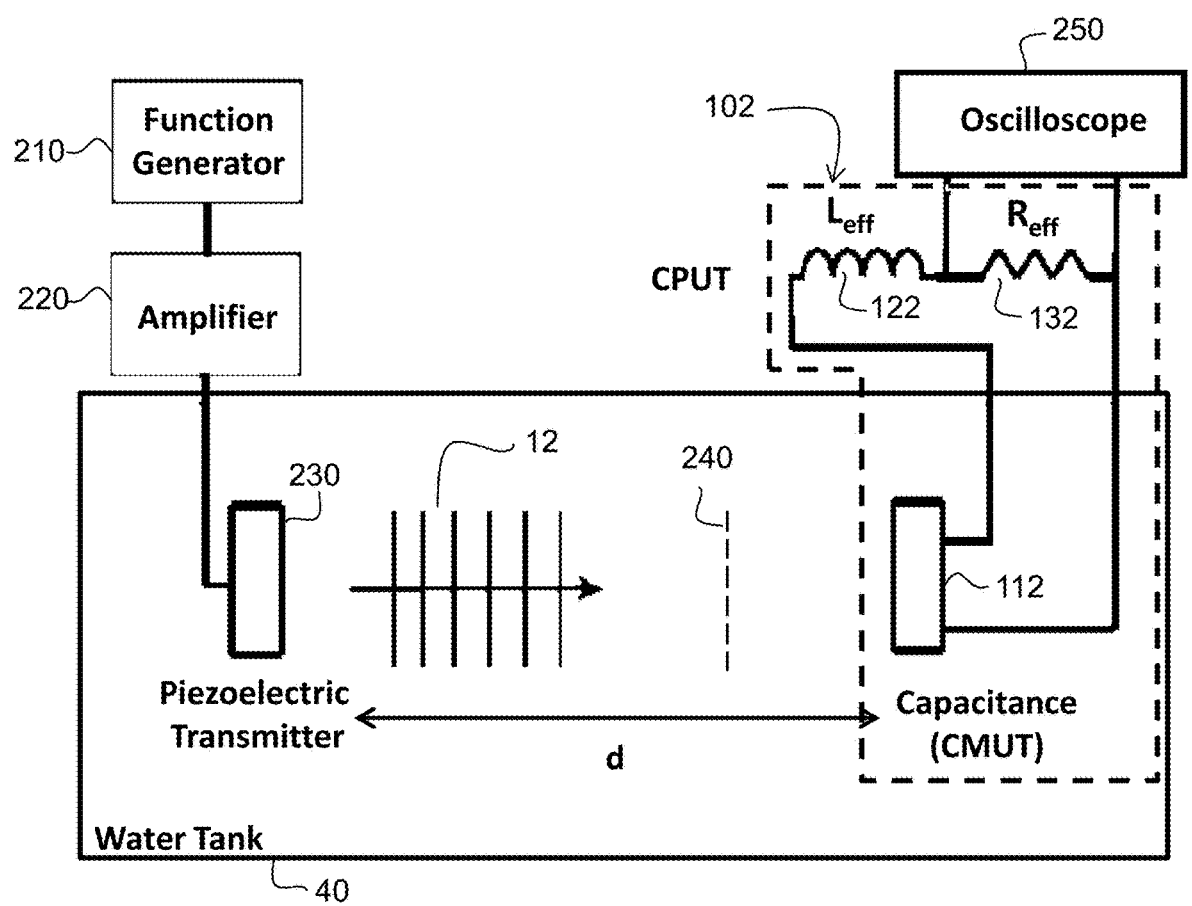
FIG. 4 illustrates an experimental setup of a proof-of-concept system according to the present invention.

FIG. 4 is a diagram of the proof-of-principal experimental setup. The CMUT 112 is wirebonded to a printed circuit board (PCB) with a 100 μH inductor 122 and a 20Ω resistor 132. The Q-factor and resonance frequency of the electrical circuit 102 with the CMUT 112 immersed in water 40 were adjusted with an operational amplifier based negative resistance circuit placed in parallel to the inductor 122 and the resistor 132 to be 130 MHz and 2.14 MHz respectively. A piezoelectric transducer 230 (Unirad 546) functioning as an ultrasonic transmitter is aligned normally to the CMUT membranes at a distance d=30 mm from the CMUT membranes to correspond to the focal length of the piezoelectric transducer 230.

A function generator 210 (Agilent 33250A) is connected to an RF power amplifier 220 (ENI 310L) which is connected to the piezoelectric transducer 230. The output across the load resistance 132 is recorded by an oscilloscope 250 (Tektronix TDS5054). A sinusoidal tone burst at 4.28 MHz ($2f_0$) is applied to the piezoelectric transducer. The duration of the tone burst is adjusted such that the end of the burst corresponds with the arrival of the ultrasound waves 12 at the surface of the CMUT 112. The time taken (t) for the wave 10 to travel the distance d is equal to d/c≈20 μs, where c=1500 m/s is the speed of sound in water. The number of cycles in the tone burst is calculated as t×2$f_0$ which is 83 cycles.

To record the response of the system with and without ultrasound pump signal 12, a plastic plate 240 that is transparent to electromagnetic waves, but which blocks the ultrasound 12 is placed between the transmitter 230 and the CMUT 112. The voltage signals across the load resistance 132 as measured by the oscilloscope 250 with and without ultrasound 12 incident on the CMUT 112 are plotted in FIGS. 5A and 5B respectively. The graphs are divided into three distinct regions. In region 1, the tone burst at 2$f_0$ is applied to the CMUT 112 and the electromagnetic signal induces oscillating electrical current in the resonator circuit 102 due to electromagnetic inductive coupling. The ultrasound signal 12 takes approximately 20 µs to travel from the source 230 to the receiver 112 through the fluid 40. The start of region 2 coincides with the arrival of the ultrasound signal 12 at the receiver 112. At this time, the electrical tone burst has ended, and only the ultrasonic excitation is present. The ultrasound forcing signal 12 impinges on the receiver 112 until the end of region 2. In region 3, the resonator circuit 102 is subjected to neither electrical nor ultrasonic excitation.

Figure 5A:
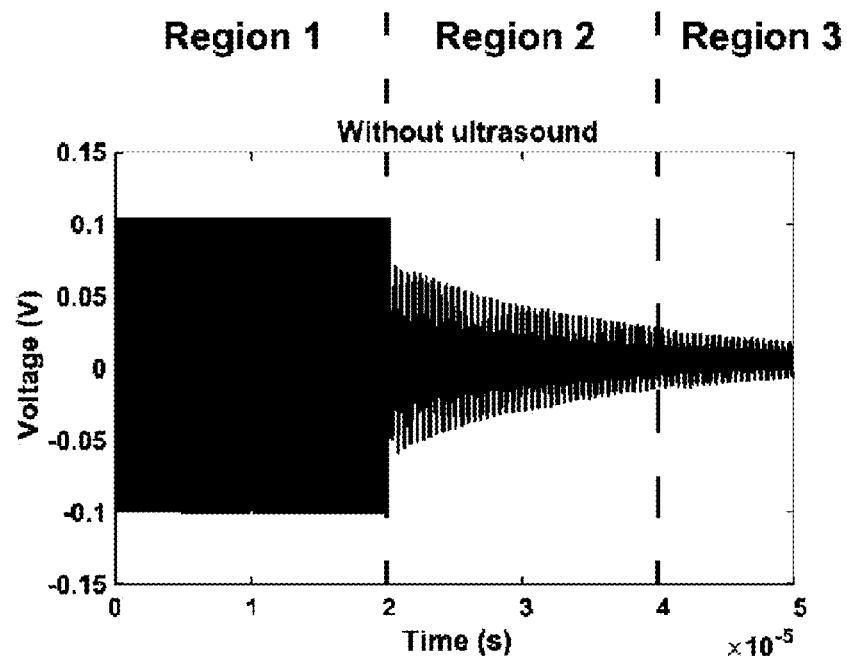
FIGS. 5A, 5B, and 6 illustrate experimental data of operational aspects of the system of FIG. 4 according to the present invention.

FIG. 5A illustrates the voltage across the load resistor 132 in the above conditions when the plastic plate 240 is placed between the piezoelectric transmitter 230 and the receiver 112. Voltage oscillations at a frequency of 2$f_0$ due to the electromagnetic coupling are measured by the oscilloscope 250 as plotted in region 1. Ultrasound 12 is blocked by the plate 240. In FIG. 5A region 2, resonance in the RLC circuit at the resonant frequency $f_0$ is excited at the start of the time period of region 2 due to electromagnetic coupling at the end of the tone burst, however in the absence of ultrasound forcing, the voltage gradually decays without any discontinuity between regions 2 and 3.

Figure 5B:
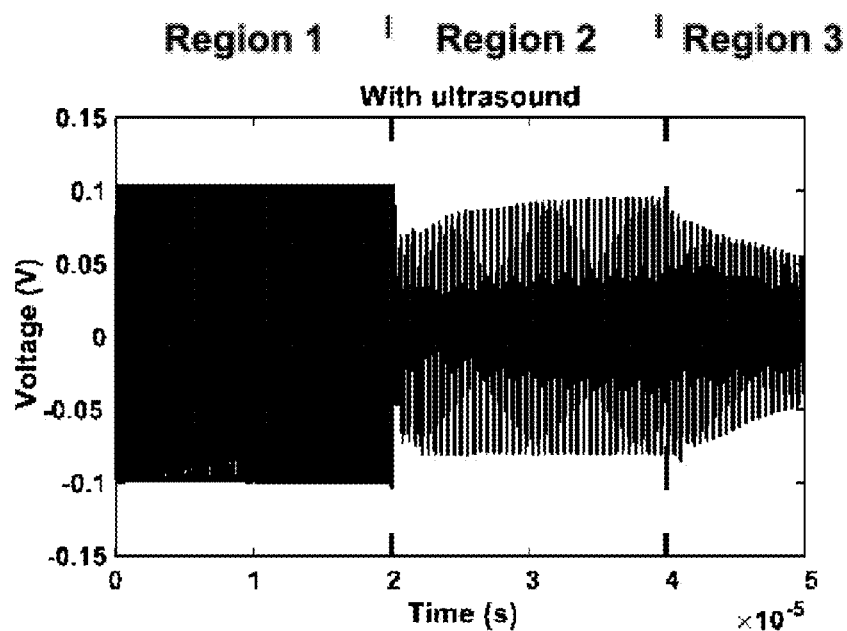

FIG. 5B illustrates the voltage across the load resistor 132 when the plastic plate 240 has been removed. Similar to FIG. 5A, region 1 of FIG. 5B is characterized by electromagnetically induced voltages at 2$f_0$. In contrast with FIG. 5A, voltage across the resistor 132 grows from the beginning to the end of region 2 as a result of ultrasonic excitation. Once the ultrasonic excitation ends at the end of region 2, the voltage begins to decay. The experimental setup thereby demonstrates that an ultrasonic source can drive a parametric resonator driven by an externally powered type modulated device into parametric resonance at a frequency $f_0$. Results in FIGS. 5A and 5B were obtained with no DC bias or permanent charge applied on the CMUT 112.

Figure 6:
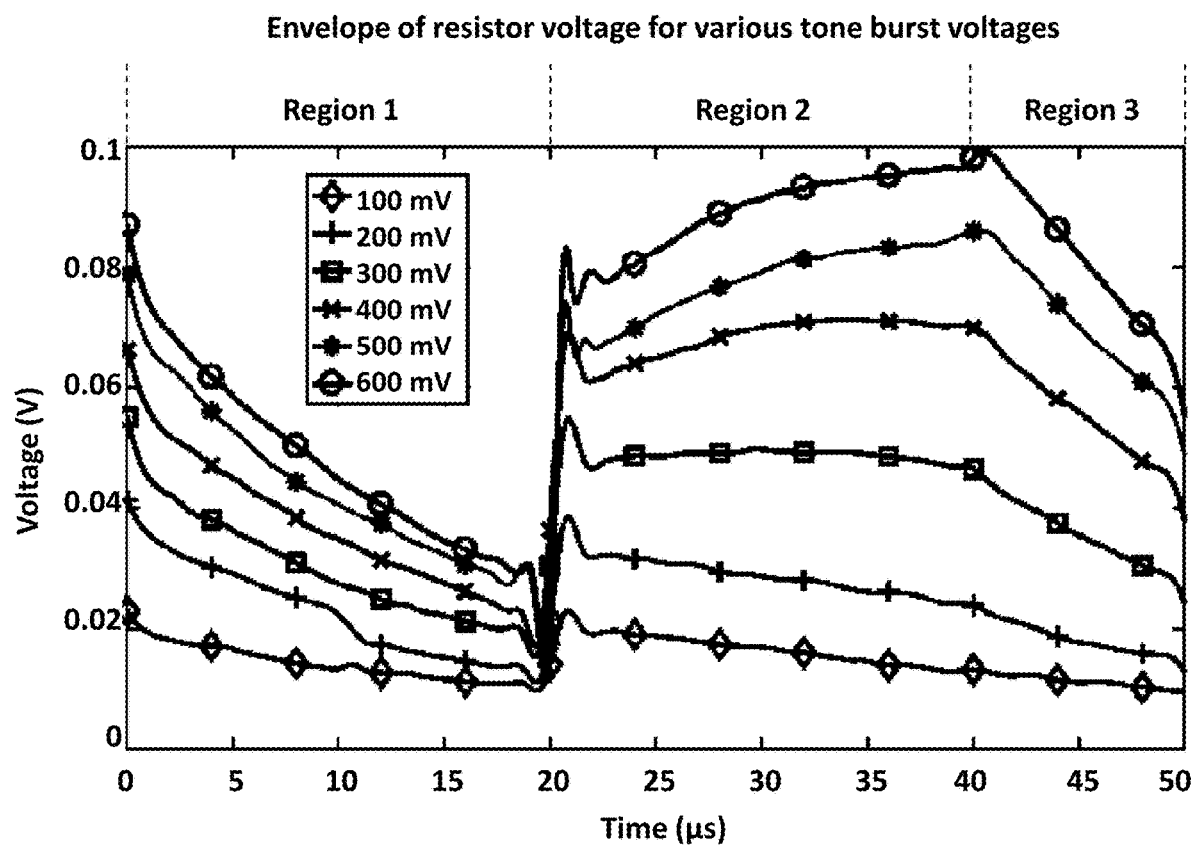

Experiments were repeated with different applied forcing amplitudes. FIG. 6 is a plot of the amplitude of the voltage across the load resistor 132 at the resonance frequency $f_0$ as a function of time where the legend indicates the amplitude of voltage applied to the piezoelectric transmitter during the tone burst. Region 1 in the plot spans from 0 to 20 µs, region 2 spans from 20 to 40 µs, and region 3 spans from 40 to 50 µs. The voltage across the load resistance 132 is filtered using an 8th order low pass Butterworth filter such that only the $f_0$ component remains. The envelope of the filtered voltage then is plotted as a function of time for various applied forcing amplitudes corresponding to various tone burst voltages. Looking at region 2, when the piezoelectric transmitter is driven by higher voltages (800 mV, 500 mV, and 400 mV), the amplitude of the voltage across the resistor increases with time as a result of parametric resonance, and when the piezoelectric transmitter 230 is driven by lower voltages (100 mV, 200 mV, and 300 mV) the amplitude of the voltage across the resistor 132 decays in region 2, with the rate of decay reducing with increased drive voltage.

The experiments demonstrate the presence of a threshold forcing amplitude, wherein if the variable parameter is oscillated within a range corresponding to an applied forcing amplitude above the threshold forcing amplitude, the resonator 102 can sustain parametric resonance oscillations. However, for applied forcing amplitudes below the threshold forcing amplitude oscillations can decay over time due to absence of a sustained parametric resonance. When the forcing signal 12 is removed as illustrated at the beginning of region 3, the voltage across the load 132 can decay over time.

The results summarized in FIGS. 5 and 6 are in qualitative agreement with the simulation results shown in FIG. 2, demonstrating predictable CPUT behavior.

Ultrasound driven parametric resonance presents a different approach to electromechanical transduction, where a modulated capacitor can be operated in the absence of an applied voltage or a permanent charge. It is contemplated that the described approach can be implemented using capacitance, inductance, and loss variations induced by ultrasound or other acoustic waves. For example, a geometry where a coil size of an inductor is changed by an incident acoustic wave, or a size of a resistor is changed by an acoustic wave can pump a parametric resonator and sustain parametric resonance. Further, the described approach could be applied to other oscillating inputs resulting in mechanical vibration of an electromechanical transducer.

The demonstrated experimental setup used a coil-wound inductor which can be too large for medical implants and other size-sensitive applications. This can be overcome by realizing that other electromechanical devices which behave like a low loss inductor in a certain frequency range can be used for compact implementations. For example, piezoelectric resonators can be used as inductors; MEMS based resonators can be used as equivalent inductors at desired low and high frequency ranges (from kHz in air to 0.1-20 MHz in immersion) for different applications; quartz resonators which have very high quality factors at low frequencies, such as 32 kHz resonators for watches can also function as an inductive circuit element at certain frequencies. Utilizing the reactive impedance of compact resonance devices within certain frequency ranges can facilitate compact parametric resonator design and may be particularly useful in parametric resonance based ultrasound transducers operated in air.

Another simulation is presented to illustrate non-linear functionality of a parametric resonator driven by an externally powered type electrical device and design considerations for the same. A one-dimensional model of a CPUT is presented and its operational characteristics are explored using Simulink.

Unlike many ultrasonic transducers which are typically operated in the linear regime, the CPUT can be more complex due to the inherent non-linearities present in the system. Performance parameters such as the acousto-electrical conversion efficiency can be strongly dependent on factors such as the medium in which the device is operated, amplitude and frequency of forcing, receiver transducer dynamics, and load resistance. These factors can all effect CPUT design considerations.

Figure 7:
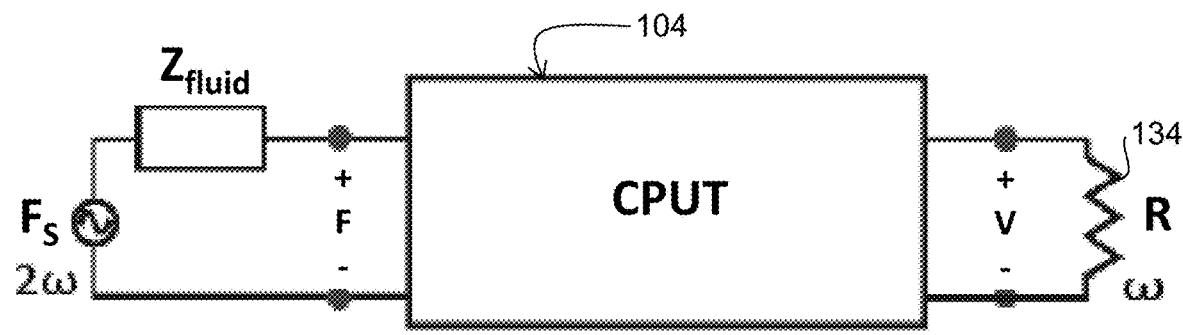
FIG. 7 illustrates a model of a system according to the present invention.
Figure 8:
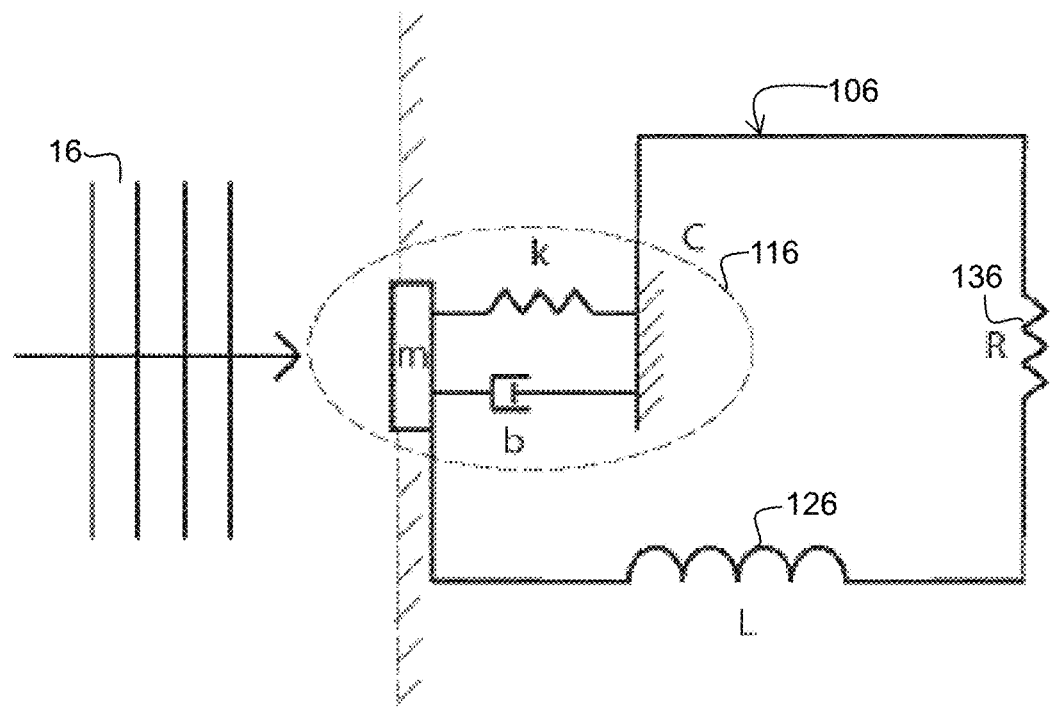
FIG. 8 illustrates a lumped parameter mechanical-to-electrical model of a system according to the present invention.

As illustrated by the electrical circuits depicted in FIGS. 7 and 8, a CPUT 104 can be considered as a black-box composed of a mechanical domain and an electrical domain. The mechanical domain can include a time-varying membrane based capacitor 116 that is excited by an incident ultrasound field 16 in a fluid. This capacitor 116 can be connected in series with an inductor 126 and a resistor 136 to form a resonant RLC circuit 106 in the electrical domain. When the capacitance is varied above a certain threshold amplitude at a frequency of about two times the resonance frequency of the RLC circuit 106, the system can be driven into parametric resonance. Once parametric resonance is established, a growing current can develop through the circuit 106 until the current is limited to a steady state value by non-linearities present in the system. In this manner, incident acoustic power can be converted by the CPUT 104 into electrical power delivered to the load resistance 134.

The CPUT can be modeled as a one-dimensional (1D) lumped parameter system as illustrated in FIG. 8. In the model, the capacitor 116 is be represented as a parallel plate piston with known mass m, stiffness k, and damping b in the 1D model. The mass and stiffness values correspond to the equivalent mass and stiffness of a membrane-based capacitor. The damping represents the radiation losses in the fluid and other mechanical damping in the system in this 1D setting. As in the simulation presented above, the effect of the fluid medium is included using the acoustic impedance for a plane wave in water ($Z_{fluid} = \rho c A$), as an approximate value. It is assumed that the mechanical losses in the capacitor are negligible when compared to the fluid losses and is hence ignored, i.e. $b = Z_{fluid}$. The incident harmonic ultrasound forcing $F_0$ at frequency $\omega_{us}$ causes the piston to oscillate with a velocity v. In order to maximize the displacement x of the piston ($x = v/j\omega$), the parameters k and m can be chosen such that the resonance frequency of the parallel plate piston is equal to the ultrasound forcing frequency, henceforth called the mechanical resonance frequency $\omega_{om}$, where $$\omega_{om} = \sqrt{\frac{k}{m}} \qquad \text{(Equation 7)}$$

The mechanical quality factor of the oscillating piston is also defined as $$Q_m = \frac{\omega_{om} m}{b} \qquad \text{(Equation 8)}$$

The same parallel plate piston can also act as a time-varying capacitor having a capacitance $$C = \frac{\varepsilon_0 A}{d_0 - x} \qquad \text{(Equation 9)}$$

where $d_0$ is the undisturbed gap between the two plates. This capacitor 116 forms part of the parametric resonator 106 along with an inductor 126 with inductance L and a load resistor 136 with resistance R. For efficient parametric excitation, the value of the inductor 126 can be chosen such that the resonant frequency of the RLC circuit is approximately half of that of the ultrasound forcing ie. $\omega_{us} = 2\omega_{oel}$. Here, $\omega_{oel}$ is the resonant frequency of the RLC circuit and can be given by, $$\omega_{oel} = \sqrt{\frac{1}{LC_0}} \qquad \text{(Equation 10)}$$

where $C_0$ is the undisturbed capacitance. Similar to Equation 8, $Q_{el}$, the electrical quality factor of the RLC circuit can be defined as $$Q_{el} = \frac{\omega_{oel} L}{R} \qquad \text{(Equation 11)}$$

The 1D lumped parameter system can also be expressed mathematically as a mechanical oscillator coupled to an electrical oscillator via a time-varying membrane based capacitor. This can be represented by two coupled non-linear ordinary differential equations:

$$\left[\frac{d^2}{dt^2} + \frac{R}{L}\frac{d}{dt} + \frac{d_0 - x}{LA\varepsilon_0}\right]V = 0 \qquad \text{(Equation 12)}$$

$$\left[\frac{d^2}{dt^2} + \frac{b}{m}\frac{d}{dt} + \frac{k}{m}\right]x = \frac{F_0}{m}\sin(\omega_{us}t) + \frac{\varepsilon_0 A}{2m}\frac{V^2}{(d_0 - x)^2} \qquad \text{(Equation 13)}$$

where the voltage across the capacitor V and displacement of the membrane x are the unknowns. As in the 1D model, R and L are the values of resistance 136 and inductance 126 in the electrical circuit. In the mechanical oscillator, the mass, stiffness, and area of the membrane are given by m, k and A, and $d_0$ is the undisturbed gap between the plates of the capacitor. The right-hand side of Equation 8 can represent the force acting on the membrane and it can be represented as the sum of the ultrasound forcing amplitude $F_0$ and the electrostatic force due to the voltage across the capacitor. This system is more complex than the parametric resonance prototype of Mathieu's Equation 7, in the sense that it is 4-dimensional ordinary differential equation system instead of a 2-dimensional ordinary differential equation system. The complexity arises from the fact that the two oscillators are non-linearly coupled and the displacement of the membrane is a function of both the forcing signal and the electrical signal generated due to this parametric excitation. The methods of solution for the two formulations are described in the following subsections.

Figure 9:
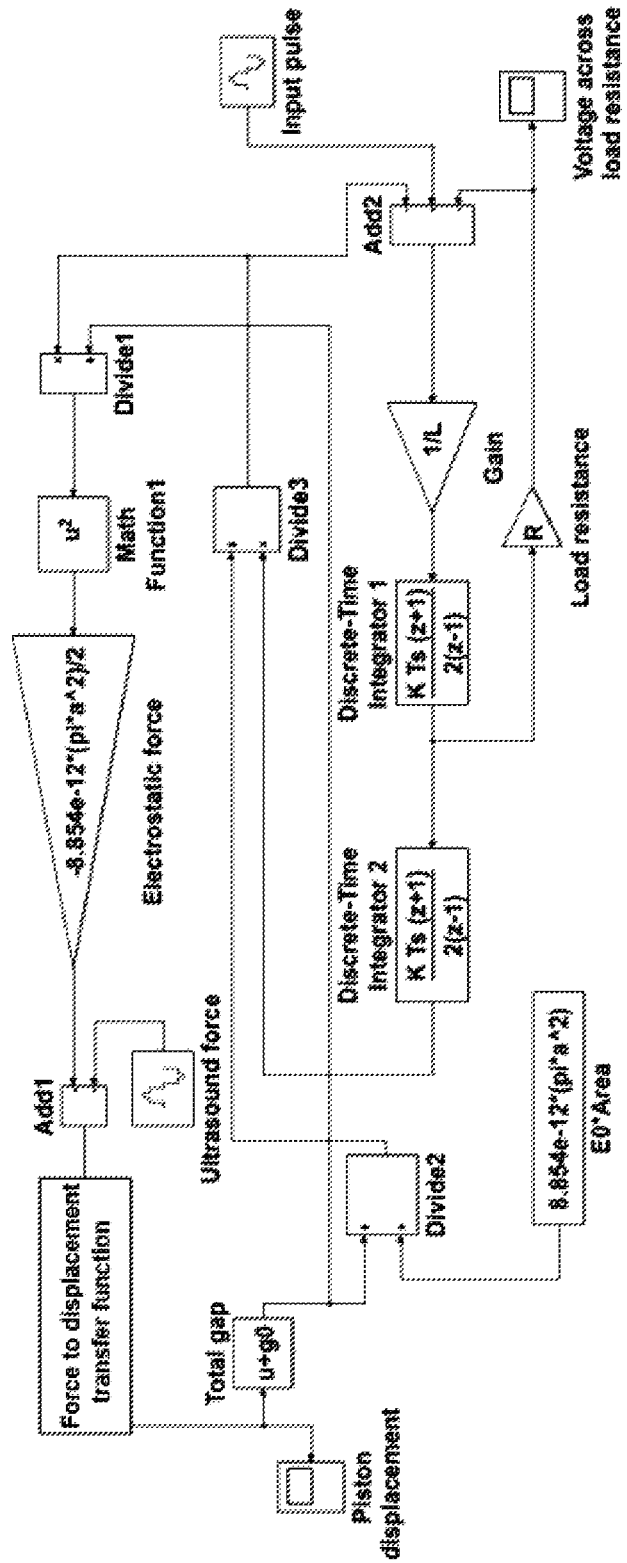
FIG. 9 illustrates a block diagram for simulating operation of a system according to the present invention.

A transient response of the 1D lumped system is analyzed in Simulink by creating a best-form mathematical model of the RLC circuit. In this case, the time-varying capacitor is represented by a block containing a transfer function that takes the voltage across the capacitor and the ultrasound force as the input and provides the parallel piston displacement as the output. The displacement can then be used to determine the instantaneous capacitance, thereby forming a closed loop—this circuit implementation is shown in FIG. 9. To provide an initial condition for parametric resonance, an electrical excitation of frequency $\omega_{oel}$ is produced in the RLC circuit by providing a short input voltage pulse. This is followed by applying a uniform ultrasound force on the face of the piston at $\omega_{us}$. If the applied forcing amplitude exceeds a threshold forcing amplitude, the CPUT can sustain parametric resonance. Parameters such as the voltage, current, and capacitor plate displacement can be recorded using the Simulink scope. It is contemplated that a constant noise source can also be used in place of the voltage pulse to demonstrate that the CPUT can work with only thermo-mechanical noise present.

As an alternative to Simulink simulations, approximate analytical solutions can be obtained by asymptotic analysis of the coupled non-linear ordinary differential equations. For this analysis, the following normalized parameters are introduced:

$$\epsilon = \frac{\mu^3 \varepsilon_0 A}{2m\xi^2}, \gamma = \frac{R}{LC\epsilon}, \alpha = \frac{1}{LA\varepsilon_0 \xi^2 \mu \epsilon}, \beta = \frac{b}{m\xi\epsilon},$$
$$F = \frac{\mu_0 F_0}{m\xi^2 \epsilon}, D = \mu d_0, \omega = \frac{\omega_{0el}}{\xi}$$
(Equation 14)

where $\xi=10^7$ and $\mu=10^8$ for experimental parameters for the purposes of demonstration. As a result, $\epsilon \ll 1$, and a nonstandard coordinate transformation is used in the demonstration to separate the timescales in the system, which can result in a more accurate approximation via the averaging theory. At steady state, the voltage amplitude V across the capacitor, oscillation amplitude of membrane displacement r, and average membrane displacement y can be expressed as:

$$V \approx \sqrt{\frac{-8D^4\alpha\beta\gamma\omega^4 + 2D^3\omega\sqrt{N}}{D^2\alpha^2\omega^2 + 16\gamma^2\omega^4 + 4\alpha\beta\gamma D\epsilon\omega^2 + \alpha^2\beta^2\epsilon^2 D^2}}$$
(Equation 15)

$$N = D^2 F^2 \alpha^4 \omega^2 + 16 F^2 \alpha^2 \gamma^2 \omega^4 -$$
$$256\beta^2\gamma^4\omega^8 + 4\alpha\beta\gamma D\omega^2(\alpha^2 F^2 - 16\beta^2\gamma^2\omega^4)\epsilon +$$
$$(D^2 F^2 \alpha^4 \beta^2 - 16D^2\alpha^2\beta^4\gamma^2\omega^4)\epsilon^2$$
(Equation 16)

$$r \approx \sqrt{\left(\frac{2\gamma\omega}{\alpha}\right)^2 + \left(\frac{\epsilon V}{4D^2\omega^2}\right)^2}$$
(Equation 17)

$$y \approx \frac{\epsilon V^2}{8D^2\omega^2}$$
(Equation 18)

Note if shorter expressions are preferred, V can be further approximated by $$V \approx \sqrt{\frac{-8D^4\alpha\beta\gamma\omega^2 + 2D^3 \sqrt{\begin{array}{c} D^2 F^2 \alpha^4 + 16F^2\alpha^2\gamma^2\omega^2 - \\ 256\beta^2\gamma^4\omega^6 \end{array}}}{D^2\alpha^2 + 16\gamma^2\omega^2}}$$
(Equation 19)

since $\epsilon \ll 1$.

TABLE I

PARAMETERS USED FOR EXAMPLE CPUT

| Symbol | Quantity | Value |
|---|---|---|
| A | Piston area | 1 mm² |
| k | Piston stiffness | 1 × 10⁸ N/m |
| m | Piston mass | 6.33 × 10⁻⁷ kg |
| $d_0$ | Vacuum gap | 120 nm |
| $\omega_{us}$ | Ultrasound frequency | 2 MHz |
| $\omega_{oem}$ | Mechanical resonance frequency | 2 MHz |
| $\omega_{oel}$ | Electrical resonance frequency | 1 MHz |
| $Z_{fluid}$ | Acoustic impedance of water | 1.5 kg/s |

Due to resistive losses in the system, it can be necessary that a change in capacitance exceed a certain minimum threshold value in order sustain parametric resonance. The minimum applied forcing amplitude required to obtain a steady state voltage can be represented as $$|F| \geq \frac{4\omega^2}{\alpha}\sqrt{\gamma^2 + 4\Delta^2\omega^2}\sqrt{\beta^2 + 16\Delta^2\omega^2}$$
(Equation 20)

in particular, if $\Delta=0$, $F_0 \geq 4\omega_{oel}^2 \text{Rb} A\epsilon_0$ where $\Delta$ is the measure of deviation of the forcing frequency from $2\omega$. From Equation 20 it can be observed that if $\Delta=0$, $F_0$ can depend only on b, R, $\omega_{oel}$ and A. In the presented 1D model, b purely depends on the medium of operation, which implies that a lower minimum force can operate in a fluid having a lower acoustic impedance. Similarly, operating the CPUT at a lower frequency also reduces the applied forcing amplitude required to sustain parametric resonance.

The CPUT can also be very sensitive to a small input force if the load resistance R and electrode area A are reduced. While this may not be practical for power transfer, where there is an optimum value of load resistance at which the impedance is matched, it may be more feasible in sensing applications, where impedance matching is typically not an issue and load resistance can be minimized to achieve high force sensitivity.

The above formulations allow one to investigate the performance of CPUTs for power transfer applications which depends on both electrical and mechanical parameters. For this purpose, the relevant performance metrics are defined and the results for a specific CPUT operating around 2 MHz in immersion are analyzed herein.

As an example, a CPUT with parameters listed in Table 1 is used to explore the device characteristics using the two models developed. In the models, the CPUT is operated in water for power transfer applications, an ultrasound frequency of 2 MHz, and a piston area of 1 mm² is chosen such that the device has a small footprint and can be operated at a reasonable depth inside water. The values of k and m are chosen such that the mechanical resonance frequency is 2 MHz and the value of the inductance is chosen such that the electrical resonance frequency is 1 MHz. Although the input ultrasound intensity is varied between 1 mW/mm² and 15 mW/mm² for the sake of simulations, the maximum FDA permissible limit of diagnostic ultrasound is 7.2 mW/mm².

The efficiency of the CPUT is a figure of merit that can be used to evaluate the transducer for power transfer applications. Using Simulink, the efficiency can be calculated as the ratio of the time averaged power dissipated across the resistor to the available acoustic power.

$$\text{efficiency} = \frac{\frac{1}{T}\int i^2 R dt}{I_{ac} \times A} \times 100(\%)$$
(Equation 21)

Here, i is the current in the circuit and R is the load resistance. $I_{ac}$ is the acoustic intensity or applied forcing amplitude of the incident ultrasound wave and is defined as $I_{ac}=p^2/2\rho c$, where p is the pressure on the face of the piston under perfectly matched impedance conditions. When the CPUT input impedance is well matched with the acoustic impedance of the fluid, most of the acoustic energy incident on the piston can pass through with minimal reflection and can be available across the load resistance as electrical power. Hence one way of achieving high efficiency can be to minimize the power reflection coefficient $|R|^2$ at the face of the piston.

$$|R|^2 = \left|\frac{Z_{fluid} - Z_{input}}{Z_{fluid} + Z_{input}}\right|^2 \qquad \text{(Equation 22)}$$

Here $Z_{fluid}$ is the acoustic impedance of the fluid 140 as defined earlier and $Z_{input}$ is the input impedance of the CPUT which can be calculated by obtaining the ratio of the complex force amplitude on the piston to the complex velocity amplitude at the face of the piston ie.

$$Z_{input} = \left.\frac{\bar{F}}{\bar{v}}\right|_{piston\ surface} \qquad \text{(Equation 23)}$$

Since $Z_{fluid}$ is fixed, one means to achieve low reflection coefficient in the bandwidth of operation is to optimize the CPUT parameter.

Figure 10:
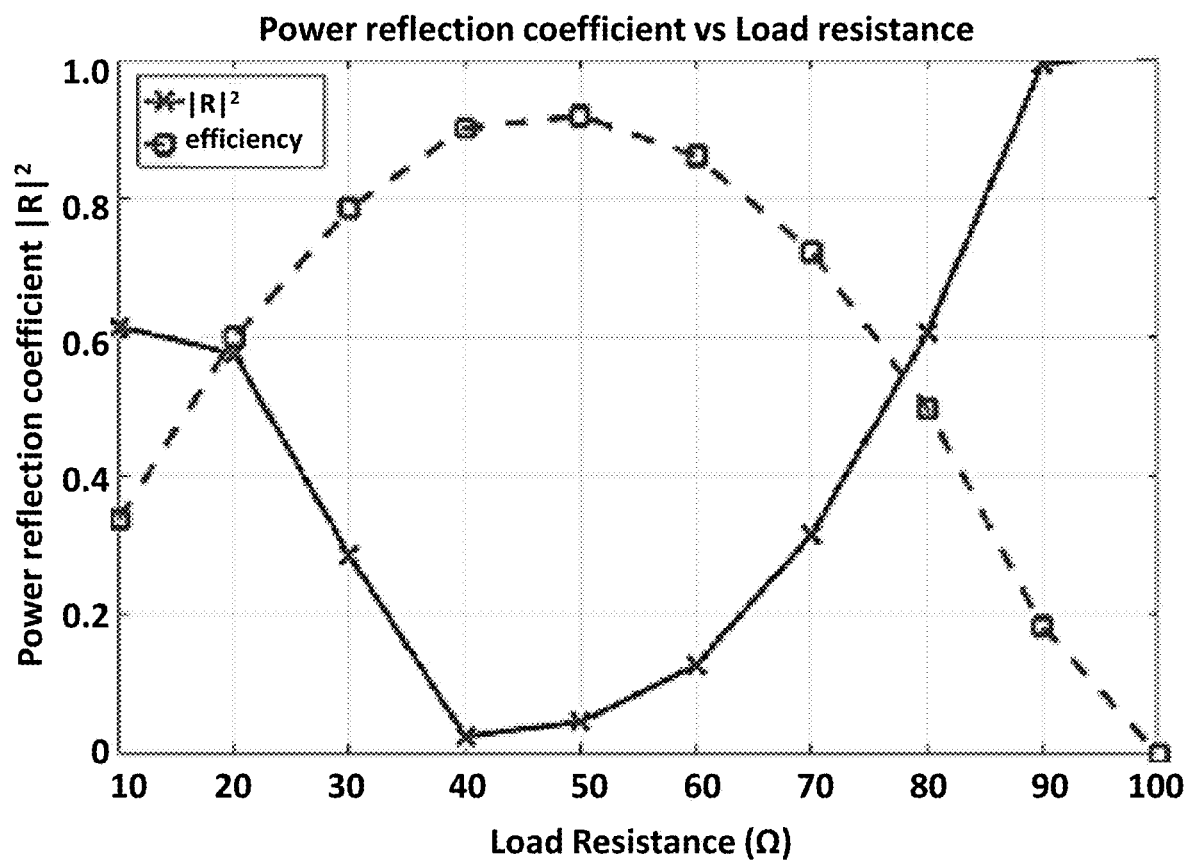
FIGS. 10-12, 13A-C, and 14-16 illustrate calculated or simulated operational aspects of a system according to the present invention.
Figure 11:
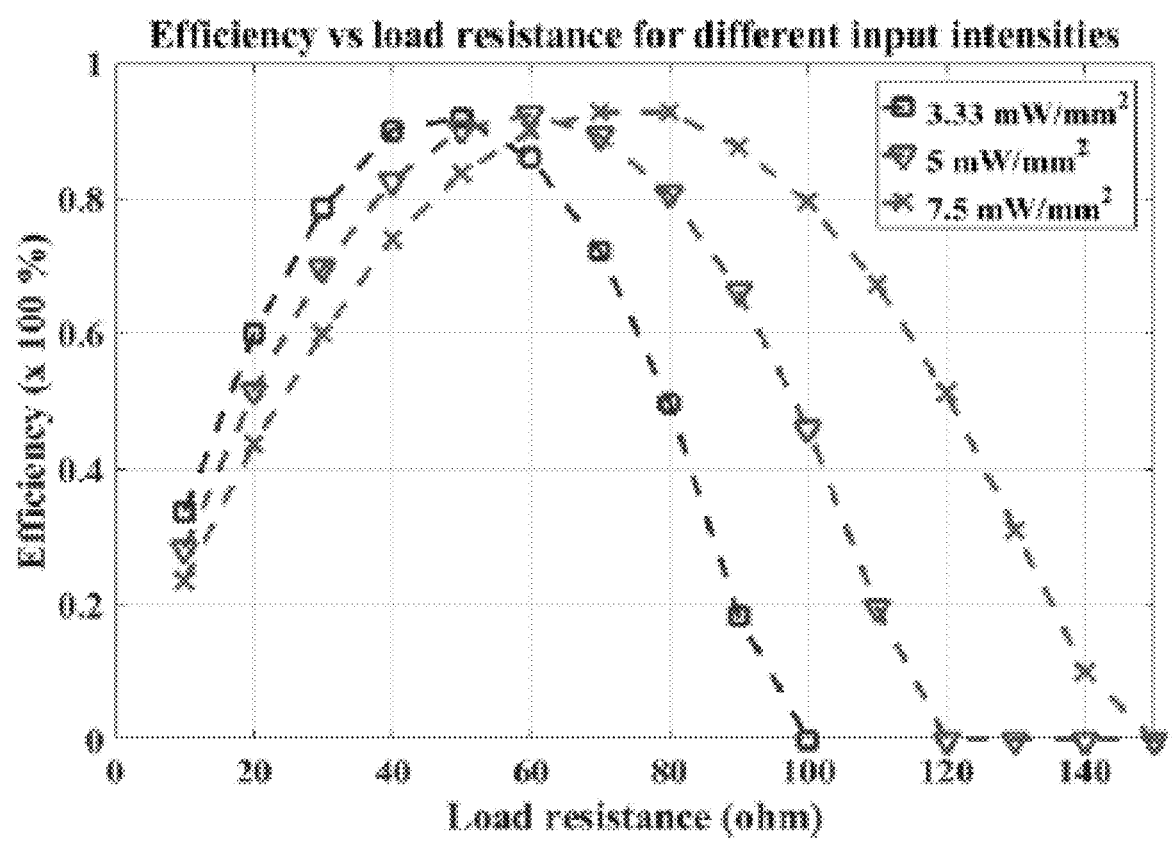

FIG. 10 is a plot showing the variation of power reflection coefficient and efficiency with load resistance for a fixed input ultrasound intensity of 3.33 mW/mm² (translates to a force of 0.1 N on a piston face having 1 mm² area) obtained using Simulink. The reflection coefficient can be large at low load resistances, can reduce until it reaches a minimum around 50Ω and then can increase again until it is maximum around 90Ω. Consistent with other results presented herein, a maximum efficiency of over 90% can be obtained when the reflection coefficient is minimum. Increasing the load resistance can cause $Z_{input}$ to change and the resistance at which maximum efficiency is obtained can correspond to the best impedance match between the CPUT and the fluid medium. As the load resistance exceeds 96Ω, in the simulated results, the efficiency drops to zero as the level of ultrasound applied forcing amplitude does not meet the required minimum threshold forcing amplitude to sustain parametric resonance as expressed, for example, in Equation 20. The upper limit of this critical load resistance can be increased further by increasing the applied forcing amplitude. As shown in FIG. 11, if the input intensity level (applied forcing amplitude) is increased, the range of load resistance in which parametric resonance is obtained, can also increase. The simulation results show that the resistance at which maximum efficiency is obtained can shift to the right (higher load resistances) with increasing applied forcing amplitudes, which implies that the input impedance of the CPUT depends on the applied forcing amplitude.

Figure 12:
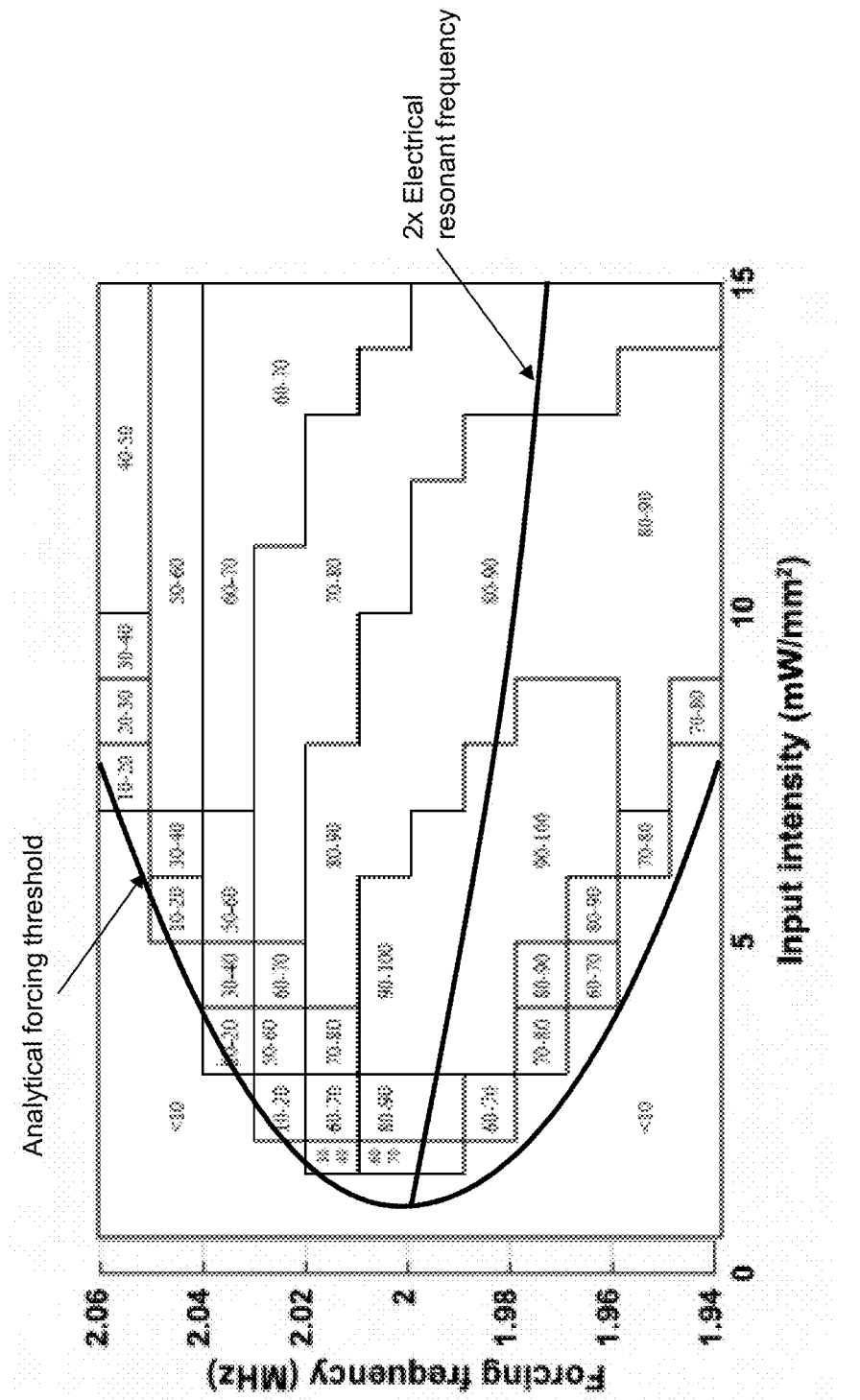

The effect of a small shift in excitation frequency on the efficiency of the CPUT is studied by varying the ultrasound applied forcing amplitude and the pump frequency at a fixed resistance of 50Ω. Using Simulink, the CPUT efficiency is simulated from input intensities ranging from 1 mW/mm² to 15 mW/mm². The ultrasound forcing frequency $\omega_{us}$ is also varied about its value of 2 MHz to study the frequency bandwidth of operation. The resulting 2D plot is shown in FIG. 12. The maximum efficiency is observed at a frequency slightly lower than 2 $\omega_{oel}$. The system can be most effectively excited into parametric resonance when the forcing frequency is two times the resonant frequency of the RLC circuit. However, as the input intensity is increased, a larger voltage can develop across the capacitor. This in turn can lead to a larger average attractive electrostatic force on the piston, thereby increasing the mean displacement y expressed in Equation 10. This can cause the capacitance of the capacitor to increase from $C_0$ to $C_0'$ thereby slightly decreasing the electrical resonance frequency to $\omega_{oel}'$. One strategy for achieving greater energy transfer efficiency is to force the capacitor at a pump frequency equal to two times $\omega_{oel}'$. By calculating the change in capacitance using the displacement data from the analytical solution, the actual $2\omega_{oel}'$ is plotted in FIG. 12. In this example simulation, the regions of maximum efficiency on the plot follow this line thereby validating this argument. Referring to FIGS. 10 and 11, one can also conclude that a better impedance match and a higher efficiency, reaching closer to 100%, could be obtained if the forcing frequency was $2\omega_{oel}'$ instead of 2 MHz.

Using Equation 20, the calculated threshold forcing amplitude is plotted as a solid line in FIG. 12. Due to the resistive loss in the RLC circuit, the apex of the curve is centered at a non-zero input intensity at 2 MHz and is symmetric on either side of the center frequency. Increasing the input intensity can cause the operational bandwidth of the CPUT to broaden. The drop in efficiency when the forcing frequency is slightly different from 2 $\omega_{oel}'$ can be less drastic at higher levels of input intensity. Thus, the simulation illustrates three design strategies for improved energy conversion efficiency: (i) load resistance can be chosen to minimize reflection at the face of the piston for a given operational input intensity; (ii) the forcing frequency can be slightly detuned to 2 $\omega_{oel}'$; and (iii) a greater input intensity can allow the CPUT to operate efficiently over a larger frequency bandwidth.

Figure 13A:
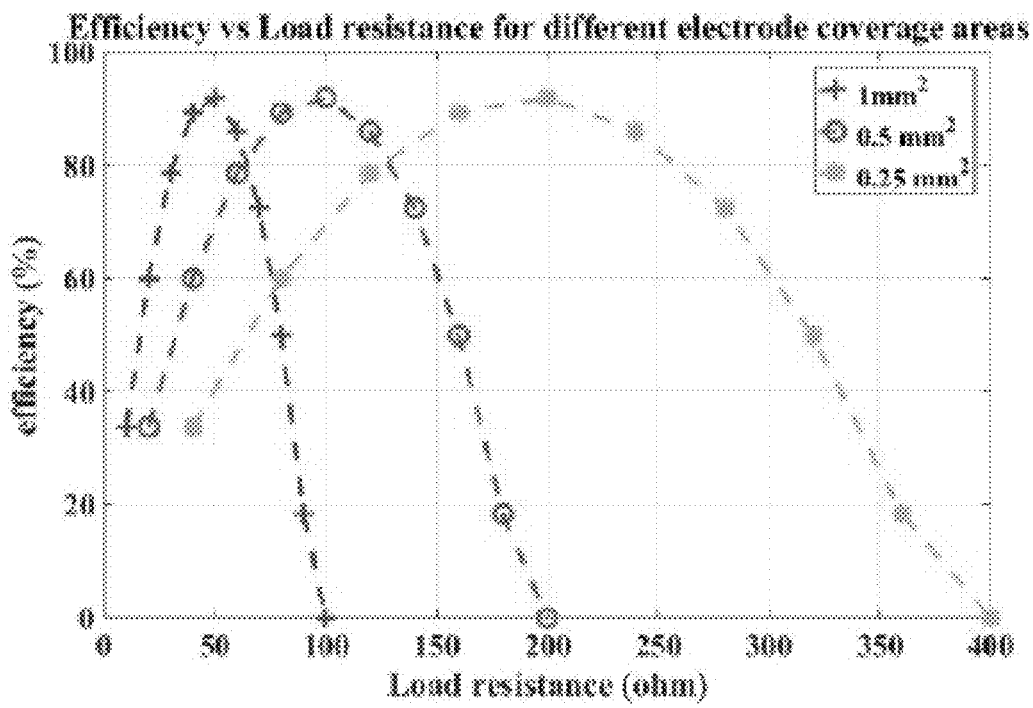

The effect of electrode coverage on the CPUT efficiency is shown in FIG. 13A for a receiver of area 1 mm² and input intensity of 3.33 mW/mm². For the same piston area, reducing the area of the electrode can have a negligible effect on the CPUT efficiency. When the electrode area is reduced, the force required to sustain parametric resonance (as expressed in Equation 20) can decrease. Thus, maintaining the same level of applied forcing amplitude while simultaneously reducing the area of the electrode can cause the critical load resistance to increase and can shift the point of maximum efficiency to the right (i.e. higher load resistance). In a practical membrane based CPUT, the average displacement can be less than the displacement of an equivalent modeled parallel plate piston as the center of the membrane can undergo a larger range of motion compared to clamped edges. A potential design strategy can include restricting the electrode coverage to the central high deflection zone to thereby compensate for the lower average displacement while still obtaining a high efficiency. Furthermore, reducing the electrode area for the same operating frequency can also increase the range of load resistance and this can provide more flexibility in design in terms of matching the CPUT to a wider range of resistive loads.

Figure 13B:
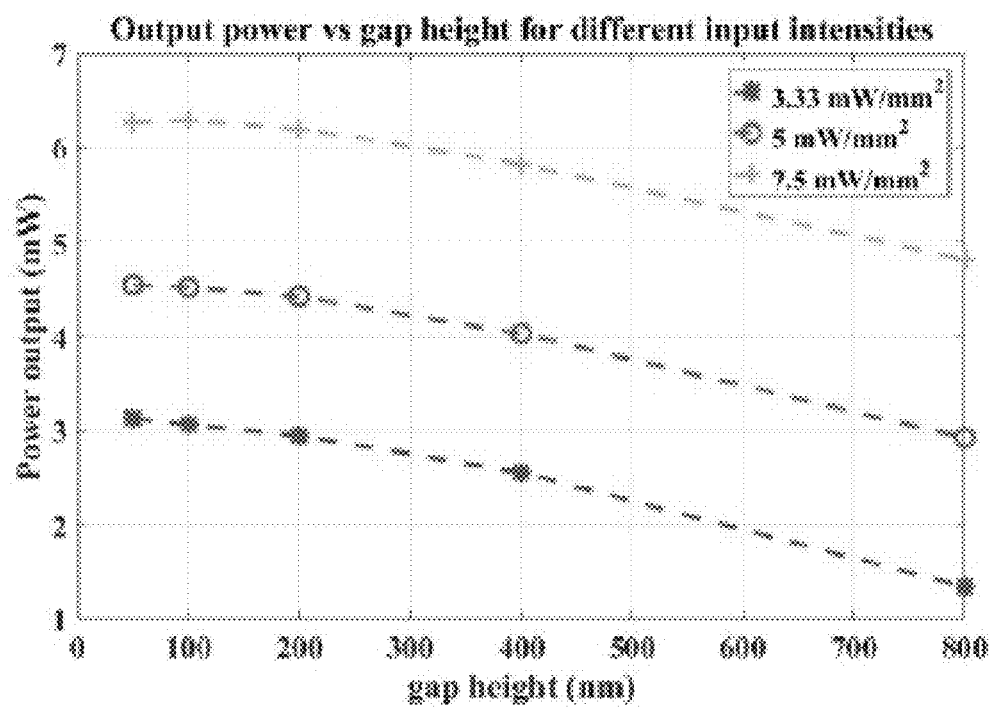
Figure 13C:
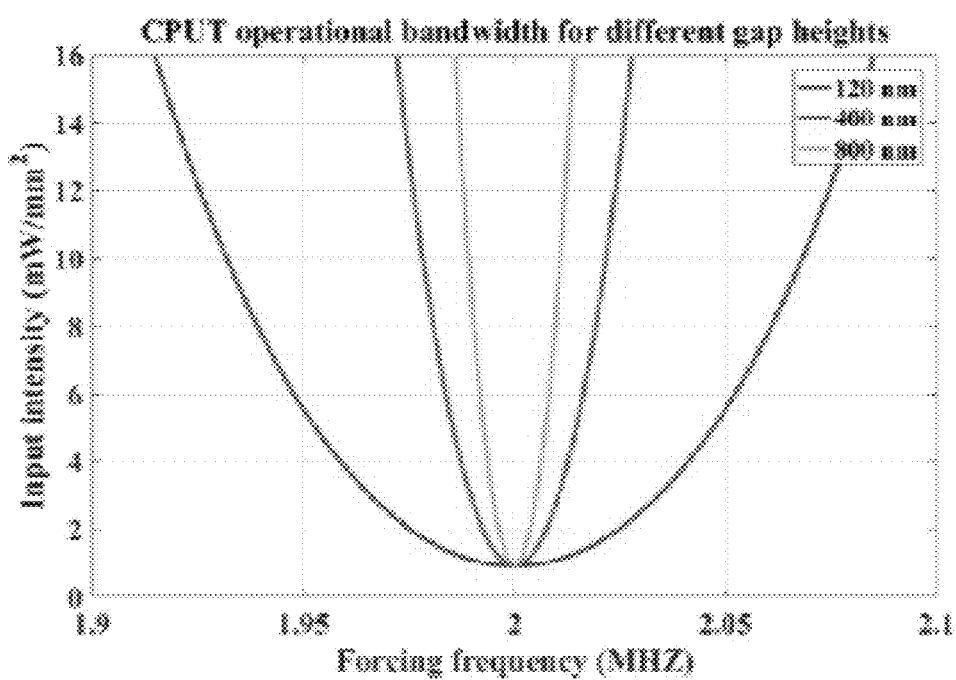

The flexibility with choosing gap height can also be considered when designing the CPUT. FIG. 13B depicts simulation results showing a variation in output power with increasing gap height at a fixed load resistance of 50Ω and an applied forcing amplitude of 3.33 mW/mm². Increasing the gap height can cause the output power to gradually decrease for different input intensities. Unlike the electrode area's relationship to critical resistance, the gap height has no such effect. Instead a decrease in gap height can cause the frequency bandwidth to decrease as illustrated in FIG. 13C; which means that at low gap heights, slight deviations from the resonant forcing frequency 2 $\omega_{oel}'$ can cause the efficiency to drastically decrease. This effect, coupled with the narrowing of bandwidth with reduced applied forcing amplitude, means that the efficiency of CPUT can drop by nearly 50% for a frequency shift of 5,000 Hz when the gap is 800 nm and the forcing is 3.33 mW/mm². Fortunately, it is typically possible to accurately control the ultrasound transmission frequency in a practical system. By controlling the ultrasound transmission frequency, CPUTs can be designed with different gap heights without compromising on the efficiency.

Figure 14:
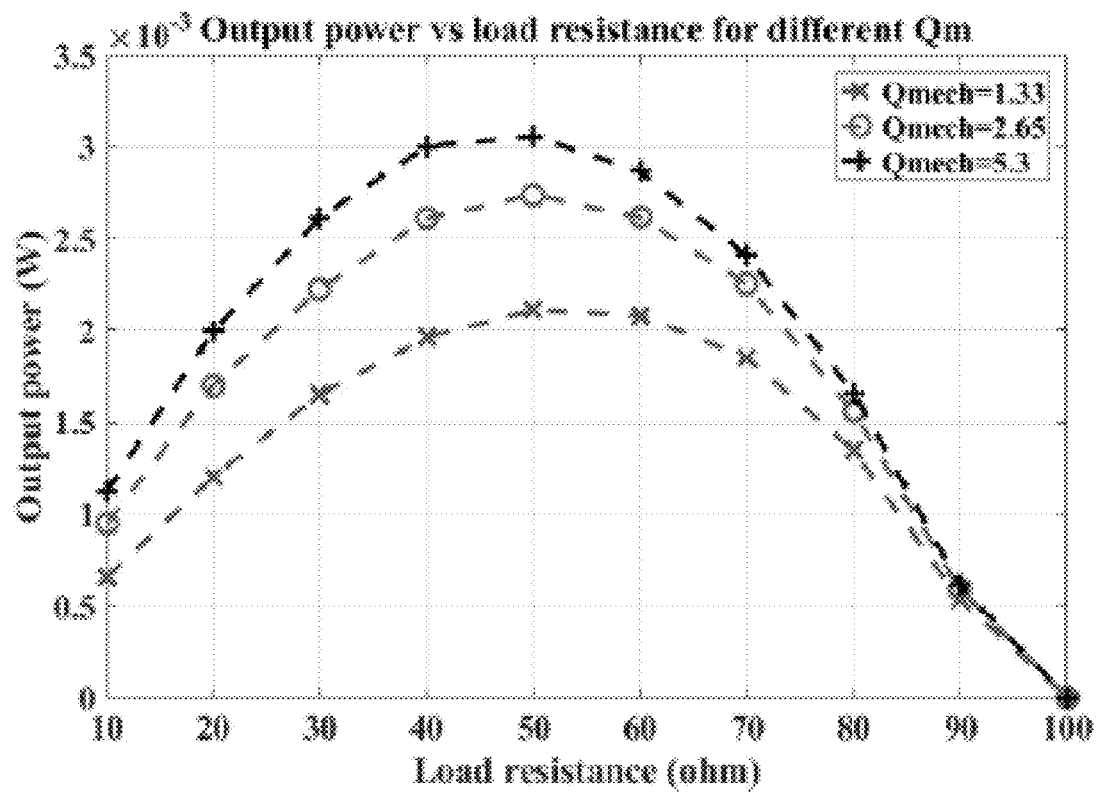
Figure 15:
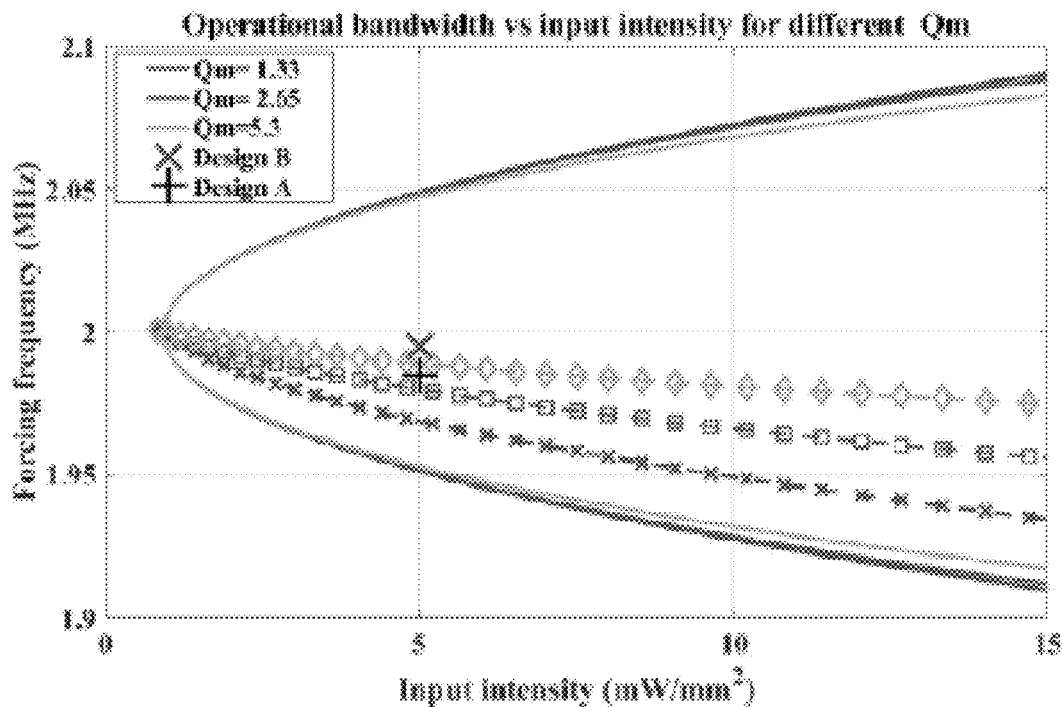

The mechanical design of the CPUT receiver (i.e. modulated device) can also be designed to optimize the CPUT for power transfer applications. For example, the receiver can be made using different structures such as a membrane, stiff plate, or interdigitated fingers, and the receiver can be made from various materials such as silicon, silicon nitride or aluminum. The mechanical Q-factor of the receiver can depend on the choice and shape of material and the fluid of operation. A potential effect of $Q_m$ on the efficiency of the simulated CPUT driven at 2 MHz at an intensity of 3.33 mW/mm$^2$ is depicted in FIG. 14. The simulation results show the CPUT having a maximum $Q_m$ of 5.3 and a maximum achievable efficiency of 92%. The maximum achievable efficiency can decrease as the Q-factor of the receiver is reduced. This drop in efficiency with reduction of Q-factor can be explained using the operational bandwidth vs. input intensity graph shown in FIG. 15. Although the simulation results illustrate that lowering of Q-factor does not necessarily affect the operational bandwidth significantly, the actual forcing pump frequency for efficient parametric resonance 2 $\omega_{oel}'$ (shown by the dashed line) shifts to a lower frequency as Q-factor is reduced. As explained previously, this can indicate that a CPUT with a low Q-factor membrane can be excited at a lower frequency in order to achieve improved power conversion efficiency. For low simulated Q-factors, 2 $\omega_{oel}'$ can be considerably different than 2 MHz, which can result in the CPUT being excited at a frequency that is considerably different from the resonance frequency. Hence the operating point of the CPUT can be considered while designing the receiver and it can be beneficial to tune it such that the receiver resonance $\omega_{om}$ is much closer to 2 $\omega_{oel}'$. This can also provide more design flexibility in designing receivers with different geometries and thicknesses without compromising on efficiency.

Figure 16:
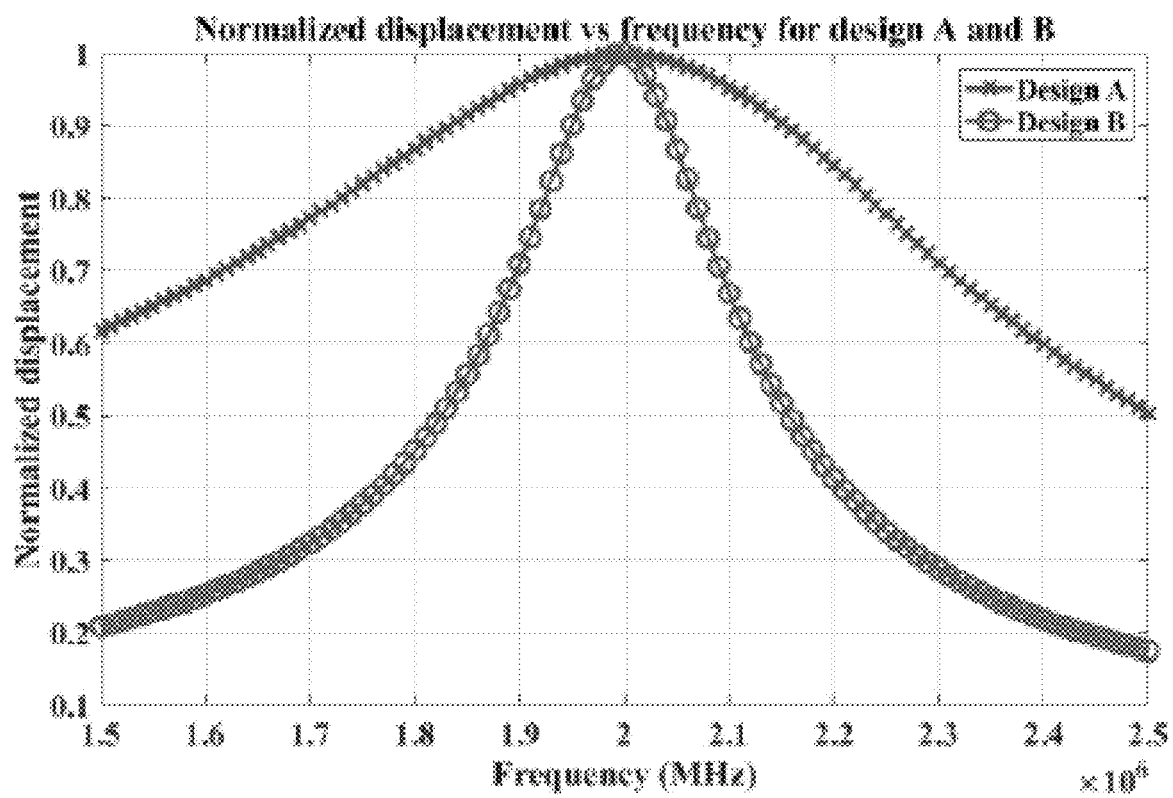

To determine the feasibility of realizing a device with similar specifications as the example simulated CPUT, two different receiver designs are simulated using COMSOL multiphysics (COMSOL inc.) for operation in water. As the aim of the study is to determine if the specifications of the example CPUT can be realized within practical dimensions, only the frequency response of the top plate in fluid is simulated. Results of the study are plotted in FIG. 16.

Design A includes a 190 µm thick single crystal silicon circular plate having an area of cross section equal to 1 mm$^2$. In this study, the resonant frequency in water is set at 2 MHz and the quality factor of the plate is determined to be approximately 3.4. An input forcing intensity of 3.33 mW/mm$^2$ is applied on the top plate and the resulting peak displacement amplitude measured at the center of the plate is 14.7 nm with an average displacement of 8 nm across the entire surface. For comparison, the displacement obtained by the parallel plate in the 1D model is 10.6 nm for the same input intensity level.

Design B includes a 260 µm thick single crystal silicon plate of radius 0.5 mm, mass loaded by a 50 µm thick plate of tungsten having radius 0.4 mm. As in Design A, the dimensions are selected such that the maximum displacement is obtained at 2 MHz. However, the increased mass of the plate produces a sharper resonance peak with a Q-factor of 10.5. By assuming the input intensity to be 5 mW/mm$^2$, we can compare these two designs with the example CPUT by noting their location in FIG. 15. Although both design A and B have a resonance frequency of 2 MHz, design A can be operated at a slightly lower frequency in order to excite parametric resonance most efficiently in the CPUT.

The value of inductance for the CPUT for increased energy conversion efficiency can be calculated as follows. The top plate of the variable capacitor can be assumed to have 100% electrode coverage. Advances in wafer bonding technology make it possible to achieve small vacuum gaps for large plate area, therefore the same gap as used for the example CPUT (120 nm) can be considered as a realistic design choice. To obtain an electrical resonance frequency of 1 MHz, a 343 µH inductor can be utilized—this can be easily realized using off the shelf wire-wound inductors. Furthermore, if the electrode area is reduced, the increased inductance can be obtained by connecting the inductors in series. Because internal resistance of the inductors add up in series they can cause a drop in power available across the load resistance. However reducing the electrode area also requires a greater value of load resistance for optimum efficiency as show in FIG. 13A, hence the value of load resistance can be much greater than the internal resistance of the inductor to maximize output power.

Next the feasibility of operating the CPUT in air is evaluated. For simulation purposes, the operating ultrasound frequency is selected to be 50 kHz. To satisfy the conditions for parametric resonance, incident acoustic forcing can satisfy the conditions expressed in Equation 20. As per OSHA guidelines, the maximum permissible ultrasound intensity in air is limited to 115 dB SPL. For a receiver of area 1 mm$^2$, this maximum intensity can translate to an incident force of roughly 1.61×10$^{-5}$N, which is approximately 5 orders of magnitude lower than that used in the water simulations. However, due to the small acoustic impedance of air as compared to water (Zair≈415 MRayl) and lower operating frequency, evaluating Equation 20 reveals that the forcing at 115 dB SPL can satisfy the inequality, thus indicating that the CPUT can work within the specified limits in air.

The displacement of the receiver due to the incident sound field can also be determined. By assuming open-circuit electrical conditions in the 1D CPUT model, the receiver displacement at mechanical resonance can be given by, $$x = \frac{2p}{\omega_{us}\rho c} \quad \text{(Equation 24)}$$

Here p is the incident pressure on the face of the receiver. Again, assuming an area of 1 mm$^2$, input force of 1.61×10$^{-5}$ and forcing frequency of 50 kHz, the displacement obtained is roughly 250 nm. In comparison, the displacement obtained in water at 2 MHz with an intensity of 3.33 mW/mm$^2$ is about 10.6 nm. Hence obtaining sufficient displacement for parametric resonance may not be a concern for air-based CPUTs. Similar to the optimization design strategies discussed herein for operation in water, the CPUT can be tailored to operate efficiently in air as a sensor or a power receiver. For operating in air, the area of the receiver can be made large enough, such that the radiation impedance seen by the CPUT is dominated by the real radiation resistance.

Examples herein include a 1D lumped parameter model to represent aspects of CPUT operation in different media. The operational characteristics of the CPUT are examined by solving the 1D model using SIMULINK and with the help of analytical solution obtained by solving the coupled nonlinear ordinary differential equations. Using a set of example parameters, the efficiency of the CPUT is evaluated for different operating parameters such as the load resistance, the frequency of operation, applied forcing amplitude, area of the electrodes, and the gap height. Two factors that can be considered to achieve optimal energy conversion efficiency are i) matching the impedance of the CPUT to the medium and ii) driving the CPUT as a frequency slightly lower than $2\omega_{oel}'$. Two different capacitor top plate designs are simulated in COMSOL to confirm that the parameters resulting from the SIMULINK simulations are practically achievable. Finally, analysis shows that although the maximum attainable applied forcing amplitude is many orders of magnitude lower in air when compared to water, the forcing amplitude can be sufficient to induce parametric resonance in a CPUT.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the disclosed technology is defined by the claims appended hereto.

The invention claimed is:

1. A parametric resonator comprising:
   an electronic device having an electrical parameter configured to oscillate at a pump frequency in response to an applied force to the electronic device;
   wherein, when the pump frequency is twice a resonance frequency of the parametric resonator, the parametric resonator is configured to:
      generate parametric resonance in response to the oscillating electrical parameter; and
      sustain an electrical signal responsive to varying the electrical parameter of the electronic device without requiring a permanent charge or a voltage applied to the electronic device;
   wherein the electronic device is a capacitor having the electrical parameter of capacitance;
   wherein the capacitance is variable in response to the applied force;
   wherein, when the pump frequency is twice a resonance frequency of the parametric resonator, the parametric resonator is further configured to sustain the electrical signal responsive to varying the capacitance of the capacitor between a first capacitance that is equal to an average capacitance plus a change in capacitance and a second capacitance that is equal to the average capacitance minus the change in capacitance; and
   wherein the change in capacitance is equal to or greater than about twice the average capacitance divided by a quality factor of the parametric resonator.

2. The parametric resonator of claim 1 further configured to generate the electrical signal responsive to varying the capacitance without requiring a permanent charge or a voltage applied to the electronic device.

3. The parametric resonator of claim 1, wherein the pump frequency is between about 16 kHz and 100 MHz.

4. The parametric resonator of claim 1, wherein the applied force is a mechanical force; and
   wherein the average capacitance is a function of the mechanical force acting to vary the capacitance of the capacitor.

5. The parametric resonator of claim 1 forming at least a portion of an implantable medical device.

6. The parametric resonator of claim 1, wherein the capacitor has a mechanical resonance frequency equal to about twice an electrical resonance frequency of the parametric resonator.

7. A parametric resonator system comprising:
   an electronic component of an RLC circuit;
   wherein the RLC circuit has a resonance frequency;
   wherein the electronic component has an electrical parameter that oscillates at a pump frequency in response to an external force;
   wherein, when the pump frequency is twice the resonance frequency of the RLC circuit, the parametric resonator system is configured to self-sustain an oscillating electrical signal in response solely to varying the electrical parameter;
   wherein the electronic component is a capacitor having the electrical parameter of capacitance;
   wherein the capacitance is variable in response to the external force;
   when the pump frequency is twice the resonance frequency of the RLC circuit, the parametric resonator system is further configured to sustain the oscillating electrical signal responsive to varying the capacitance of the capacitor between a first capacitance that is equal to an average capacitance plus a change in capacitance and a second capacitance that is equal to the average capacitance minus the change in capacitance; and
   wherein the change in capacitance is equal to or greater than about twice the average capacitance divided by a quality factor of the parametric resonator system.

8. The parametric resonator system of claim 7, wherein the system is configured to self-sustain the oscillating electrical signal without requiring an electrical power source selected from the group consisting of a DC bias, an electrical charge, and external electrical power source.

9. The parametric resonator system of claim 8, wherein the pump frequency is between about 16 kHz and 100 MHz.

10. The parametric resonator system of claim 9, wherein the capacitor is a modulated capacitor.

11. The parametric resonator system of claim 10, wherein the parametric resonator system is configured to sustain the oscillating electrical signal in response to varying the capacitance of the modulated capacitor with the application of an acoustic signal at the pump frequency to the modulated capacitor.

12. The parametric resonator system of claim 11, wherein the pump frequency of the acoustic signal is about twice a frequency of the oscillating electrical signal.

13. The parametric resonator system of claim 7 further comprising:
the RLC circuit; and
a transmitter for transmitting the external force at the pump frequency.

14. A method for electrical transduction comprising:
generating parametric resonance in a parametric resonator in response to an applied force to an electronic component of the parametric resonator oscillating an electrical parameter of the electronic component of the parametric resonator; and
sustaining the parametric resonance in the parametric resonator solely by the applied force oscillating the electrical parameter of the electronic component;
wherein a transmitter transmitting the applied force to the electronic component is in wireless communication with the electronic component;
wherein the oscillating electrical parameter has a pump frequency that is twice a resonance frequency of the parametric resonator;
wherein the electronic component is a capacitor having the electrical parameter of capacitance;
wherein the capacitance is variable in response to the applied force;
wherein the method further comprises sustaining the parametric resonance responsive to varying the capacitance of the capacitor between a first capacitance that is equal to an average capacitance plus a change in capacitance and a second capacitance that is equal to the average capacitance minus the change in capacitance; and
wherein the change in capacitance is equal to or greater than about twice the average capacitance divided by a quality factor of the parametric resonator.

15. The method of claim 14, wherein the applied force is a mechanical force.

16. The method of claim 15 further comprising:
applying the applied force to the capacitor;
oscillating the capacitance of the capacitor at the pump frequency in response to the mechanical force; and
generating an initial oscillation through inductive coupling of the parametric resonator with an electromagnetic signal.

17. A parametric resonator comprising a capacitive component having a capacitance that varies in response to an external force;
wherein the parametric resonator is configured to sustain an oscillating electrical signal in response to varying the capacitance of the capacitive component with the application of an acoustic signal to the capacitive component, without requiring an electrical power source;
wherein the acoustic signal varies the capacitance of the capacitive component between a first capacitance that is equal to an average capacitance plus a change in capacitance and a second capacitance that is equal to the average capacitance minus the change in capacitance; and
wherein the change in capacitance is equal to or greater than about twice the average capacitance divided by a quality factor of the capacitive component.

18. The parametric resonator of claim 17, wherein the parametric resonator is further configured to oscillate the electrical signal at a resonance frequency responsive to varying the capacitance at a pump frequency that is about twice the resonance frequency.

19. The parametric resonator of claim 18, wherein the pump frequency is between about 16 kHz and 100 MHz.

20. The parametric resonator of claim 17, wherein a frequency of the acoustic signal is about twice a frequency of the oscillating electrical signal.

* * * * *